US 11,858,962 B2

United States Patent
Anstrom et al.

(10) Patent No.: US 11,858,962 B2
(45) Date of Patent: Jan. 2, 2024

(54) POLYPEPTIDES USEFUL FOR DETECTING ANTI-RHABDOVIRUS ANTIBODIES

(71) Applicant: Boehringer Ingelheim Vetmedica GmbH, Ingelheim am Rhein (DE)

(72) Inventors: David Anstrom, Ames, IA (US); Eric Martin Vaughn, Ames, IA (US); Arun V. Iyer, Ames, IA (US); Michael B. Roof, Ames, IA (US)

( * ) Notice: Subject to any disclaimer, the term of this patent is extended or adjusted under 35 U.S.C. 154(b) by 124 days.

(21) Appl. No.: 17/168,439

(22) Filed: Feb. 5, 2021

(65) Prior Publication Data

US 2021/0246171 A1    Aug. 12, 2021

Related U.S. Application Data

(60) Provisional application No. 62/970,873, filed on Feb. 6, 2020.

(51) Int. Cl.
| | | |
|---|---|---|
| *C07K 14/005* | (2006.01) | |
| *C12N 7/00* | (2006.01) | |
| *G01N 33/569* | (2006.01) | |

(52) U.S. Cl.
CPC .............. *C07K 14/005* (2013.01); *C12N 7/00* (2013.01); *G01N 33/56983* (2013.01); *C07K 2319/30* (2013.01); *C12N 2760/20022* (2013.01); *G01N 2333/145* (2013.01); *G01N 2469/20* (2013.01)

(58) Field of Classification Search
CPC .............. C07K 14/005; C07K 2319/30; C07K 2319/00; C07K 2319/21; C07K 2319/50; C12N 7/00; C12N 2760/20022; C12N 2710/14043; C12N 2710/14143; G01N 33/56983; G01N 2333/145; G01N 2469/20
See application file for complete search history.

(56) References Cited

U.S. PATENT DOCUMENTS

| | | | | |
|---|---|---|---|---|
| 6,497,873 | B1 * | 12/2002 | Whitt ...................... | A61P 33/00 435/235.1 |
| 6,524,572 | B1 * | 2/2003 | Li ......................... | C07K 14/705 435/235.1 |
| 7,514,543 | B2 * | 4/2009 | Massberg ................... | A61P 9/10 536/23.1 |
| 9,347,951 | B2 * | 5/2016 | Kaplan ................. | C07K 14/005 |
| 9,409,987 | B2 * | 8/2016 | Toporik .................... | A61P 31/00 |
| 2010/0322929 | A1 * | 12/2010 | Zurawski ....... | A61K 39/001129 435/69.6 |
| 2020/0216502 | A1 * | 7/2020 | Albertini ................... | C12N 7/00 |
| 2021/0024615 | A1 * | 1/2021 | Pleass .................... | C07K 16/00 |
| 2021/0122805 | A1 * | 4/2021 | Camphausen ......... | C07K 14/78 |

FOREIGN PATENT DOCUMENTS

| | | |
|---|---|---|
| WO | 2016141338 A2 | 9/2016 |
| WO | 2018176103 A1 | 10/2018 |
| WO | WO-2018176103 A1 * | 10/2018 .............. A61P 31/14 |
| WO | 2015051255 A1 | 4/2021 |

OTHER PUBLICATIONS

Czajkowsky DM, Hu J, Shao Z, Pleass RJ. Fc-fusion proteins: new developments and future perspectives. EMBO Mol Med. Oct. 2012;4(10):1015-28. Epub Jul. 26, 2012. (Year: 2012).*
Dietzschold B, Wunner WH, Wiktor TJ, Lopes AD, Lafon M, Smith CL, Koprowski H. Characterization of an antigenic determinant of the glycoprotein that correlates with pathogenicity of rabies virus. Proc Natl Acad Sci U S A. Jan. 1983;80(1):70-4. (Year: 1983).*
Luo J, Zhang B, Wu Y, Guo X. Amino Acid Mutation in Position 349 of Glycoprotein Affect the Pathogenicity of Rabies Virus. Front Microbiol. Apr. 3, 2020;11:481. (Year: 2020).*
Kazuhisa Nakayama, Furin: a mammalian subtilisin/Kex2p-like endoprotease involved in processing of a wide variety of precursor proteins, Biochem, J., 1997, 327, 625-235.
Michael Cieplik, Hans-Dieter Klenk and Wolfgang Garten, Identification and Characterization of Spodoptera frugiperda Furin: A Thermostable Subtilisin-Like Endoprotease, Biol. Chem., Dec. 1998, vol. 379, pp. 1433-1440.
Peter Duckert, Sùren Brunak and Nikolaj Blom, Prediction of proprotein convertase cleavage sites, Protein Engineering, Design & Selection, 2004, vol. 17 No. 1 pp. 107-112.
Hailun MA, Teresa A. Galvin, Dustin R. Glasner, Syed Shaheduzzaman, Arifa S. Khan, Identification of a Novel Rhabdovirus in Spodoptera frugiperda Cell Lines, Jun. 2014, Journal of Virology, 88, 12, p. 6576-6585.
Jasjit Joahl et al., "Antigenic characterization of bovine ephemeral fever rhabdovirus G and GNS glycoproteins expressed from recombinant baculovirus," Archives of Virology, Official Journal of the Virology Division of the International Union of Microbiological Societies, Springer-Verlag, VI, vol. 153, No. 9, Jul. 15, 2008, pp. 1657-1665.
Czajkowsky Daniel M. et al., "Fc-fusion proteins: new developments and future perspectives". EMBO Molecular Medicine, vol. 4, No. 10, Oct. 1, 2012, pp. 1015-1028.
Sliepen Kwinten et al., "Immunosilencing a Highly Immunogenic Protein Trimerization Domain", Journal of Biological Chemistry, vol. 290, No. 12, Jan. 29, 2015, pp. 7436-7442.

* cited by examiner

*Primary Examiner* — Rachel B Gill
(74) *Attorney, Agent, or Firm* — Suzanne Seavello Shope

(57) ABSTRACT

The present invention relates to recombinantly constructed proteins useful for analytical assays, in particular for determining in a biological sample obtained from an individual the presence of antibodies specific for a rhabdovirus. More particular, the present invention relates to a polypeptide comprising an ectodomain of a rhabdovirus glycoprotein and a heterologous multimerization domain linked to said ectodomain. In one example, a fusion protein of the formula x-y-z is provided, wherein x consists of or comprises such an ectodomain being optionally free of a furin cleavage site, y is a linker moiety, and z is a heterologous multimerization domain optionally selected from the group consisting of immunoglobulin sequence, coiled coil sequence, streptavidin sequence, fibritin sequence, and avidin sequence.

16 Claims, No Drawings

Specification includes a Sequence Listing.

SEQUENCE LISTING

```
<160> NUMBER OF SEQ ID NOS: 25

<210> SEQ ID NO 1
<211> LENGTH: 529
<212> TYPE: PRT
<213> ORGANISM: Artificial Sequence
<220> FEATURE:
<223> OTHER INFORMATION: ectodomain of SFRV glycoprotein variant

<400> SEQUENCE: 1

Asn Pro Leu Ser Tyr Pro Asn Gly Ile Leu Thr Asn Asn Ser Thr His
1               5                   10                  15

Asn His Pro Leu Ser Asp Phe Tyr Ile Phe Tyr Glu Asn Ser Ser Leu
            20                  25                  30

Thr Tyr Thr Gln Phe Pro Val Ala Pro Asp Cys Ser Ser Ile Leu Asp
        35                  40                  45

Thr Arg Asp Glu Gln Tyr Pro Thr Thr Val Thr Leu Trp Lys Val Asp
```

```
            50                  55                  60
Gln Glu Ser Gln Ala Glu Trp Gly Leu Leu Leu Trp Gln Glu Arg Ile
 65                  70                  75                  80

Asp Thr Thr Cys Ser Trp Asn Phe Trp Gly Asn Tyr Lys Gly Ser Ile
                 85                  90                  95

Val Ser Lys Ser Ser Val Pro Leu Lys Asp Ile Pro Ser Gly Ser Ala
            100                 105                 110

Arg Asn Gly Tyr Trp Ala Leu Ser Asn Asp Glu Val Gln Glu Ile Asp
        115                 120                 125

His Val Pro Tyr Asn Leu Arg Tyr Tyr Cys Tyr Trp Cys Arg Asn Glu
    130                 135                 140

Tyr Pro Gly Ser Phe Tyr Met Arg Tyr Val Lys Lys Val Arg Ile Ile
145                 150                 155                 160

Arg Asn Pro Asp Gly Ser Ile Lys Thr Pro Arg Gly Ser Trp Val His
                165                 170                 175

Glu Leu Asp Asn Leu Trp Gly Asp Gln Met Arg Tyr Leu Val Ile Arg
            180                 185                 190

Arg Phe Gly Gly Glu Ser Ser Cys Pro Leu Lys Ile Tyr Asp Val Arg
        195                 200                 205

Ala Gly Val Leu Ser Lys Ser Arg Ser Asn Phe Ile Leu Val Ser Leu
    210                 215                 220

Pro Ser Leu Asn Leu Gln Phe Ser Val Ser Leu Glu Ser Thr Glu Thr
225                 230                 235                 240

Lys Cys Ser Phe Gly Asp Lys Thr Tyr Asp Ile Val Gln Ser Met Gly
                245                 250                 255

Gly Tyr Leu Leu Ser Ile Asp Ile Gly Asn Ala Asn Trp Arg Gly Pro
            260                 265                 270

Trp Asp Pro Thr Pro Gln His Pro Gly Arg Glu Arg Gln Ser Ile Met
        275                 280                 285

Glu Phe Pro Asp Gln Thr Ser Phe Arg Tyr Asn Gln Phe Ile Asn Tyr
    290                 295                 300

His Ser Ser Pro Arg His Lys Gln His Asp Gln Glu Phe Glu Phe Pro
305                 310                 315                 320

Leu Ser Leu Lys Ser Ser Tyr Asp Tyr Ala Gln Phe Arg Tyr Glu Gln
                325                 330                 335

Asn Phe Ile Ile Arg Gln Ile Asn Lys Asn Phe Gly Leu Leu Gln Lys
            340                 345                 350

Ser Ile Cys Asp Ile Gln Phe Ser Lys Trp Gln Asn Leu Ser Pro Pro
        355                 360                 365

Asn Leu Ala Met Lys Ile Ala His Tyr Val Thr Gly Ser Ile His Ser
    370                 375                 380

Ile Gly Gly Val His His Gly Ser Tyr Ser Ile Gln Arg Thr Glu Lys
385                 390                 395                 400

Ser Ile Thr Lys Val Asn Leu Val Phe Pro Ile Val Ile Val His Gly
                405                 410                 415

Met Tyr Lys Cys Gln Arg Glu Pro Ser Lys Glu Val Val Trp Ala Glu
            420                 425                 430

Pro Val Thr Gly Ile Leu Phe Lys Ser Pro Ile Pro Thr His Phe Ser
        435                 440                 445

Leu Ser Ser Ser Trp Leu Pro Gly Val Asn Gly Ser Ser Ile Val Pro
    450                 455                 460

Leu Thr Gly Gln Ile Leu Leu Pro Glu Ile Thr Met Asp His Leu Glu
465                 470                 475                 480
```

```
Val Val Gln Gln Val Glu Ala Lys Met Val Lys Ser Met Tyr Thr Asn
            485                 490                 495

Val Glu Leu Phe Gly Ser Thr Glu Glu Phe Gln Arg Tyr Gln Thr Gln
            500                 505                 510

Gly Ile Thr Ser Asp Glu Gln Ser Asn Thr Val Asn Pro Trp Ile Gly
            515                 520                 525

Leu

<210> SEQ ID NO 2
<211> LENGTH: 530
<212> TYPE: PRT
<213> ORGANISM: Artificial Sequence
<220> FEATURE:
<223> OTHER INFORMATION: ectodomain of SFRV glycoprotein variant

<400> SEQUENCE: 2

Ser Asn Pro Leu Ser Tyr Pro Asn Gly Ile Leu Thr Asn Asn Ser Thr
1               5                   10                  15

His Asn His Pro Leu Ser Asp Phe Tyr Ile Phe Tyr Glu Asn Ser Ser
            20                  25                  30

Leu Thr Tyr Thr Gln Phe Pro Val Ala Pro Asp Cys Ser Ser Ile Leu
            35                  40                  45

Asp Thr Arg Asp Glu Gln Tyr Pro Thr Thr Val Thr Leu Trp Lys Val
50                  55                  60

Asp Gln Glu Ser Gln Ala Glu Trp Gly Leu Leu Leu Trp Gln Glu Arg
65                  70                  75                  80

Ile Asp Thr Thr Cys Ser Trp Asn Phe Trp Gly Asn Tyr Lys Gly Ser
            85                  90                  95

Ile Val Ser Lys Ser Ser Val Pro Leu Lys Asp Ile Pro Ser Gly Ser
            100                 105                 110

Ala Arg Asn Gly Tyr Trp Ala Leu Ser Asn Asp Glu Val Gln Glu Ile
            115                 120                 125

Asp His Val Pro Tyr Asn Leu Arg Tyr Tyr Cys Tyr Trp Cys Arg Asn
            130                 135                 140

Glu Tyr Pro Gly Ser Phe Tyr Met Arg Tyr Val Lys Lys Val Arg Ile
145                 150                 155                 160

Ile Arg Asn Pro Asp Gly Ser Ile Lys Thr Pro Arg Gly Ser Trp Val
            165                 170                 175

His Glu Leu Asp Asn Leu Trp Gly Asp Gln Met Arg Tyr Leu Val Ile
            180                 185                 190

Arg Arg Phe Gly Gly Glu Ser Ser Cys Pro Leu Lys Ile Tyr Asp Val
            195                 200                 205

Arg Ala Gly Val Leu Ser Lys Ser Arg Ser Asn Phe Ile Leu Val Ser
            210                 215                 220

Leu Pro Ser Leu Asn Leu Gln Phe Ser Val Ser Leu Glu Ser Thr Glu
225                 230                 235                 240

Thr Lys Cys Ser Phe Gly Asp Lys Thr Tyr Asp Ile Val Gln Ser Met
            245                 250                 255

Gly Gly Tyr Leu Leu Ser Ile Asp Ile Gly Asn Ala Asn Trp Arg Gly
            260                 265                 270

Pro Trp Asp Pro Thr Pro Gln His Pro Gly Arg Glu Arg Gln Ser Ile
            275                 280                 285

Met Glu Phe Pro Asp Gln Thr Ser Phe Arg Tyr Asn Gln Phe Ile Asn
            290                 295                 300
```

-continued

```
Tyr His Ser Ser Pro Arg His Lys Gln His Asp Gln Glu Phe Glu Phe
305                 310                 315                 320

Pro Leu Ser Leu Lys Ser Ser Tyr Asp Tyr Ala Gln Phe Arg Tyr Glu
            325                 330                 335

Gln Asn Phe Ile Ile Arg Gln Ile Asn Lys Asn Phe Gly Leu Leu Gln
        340                 345                 350

Lys Ser Ile Cys Asp Ile Gln Phe Ser Lys Trp Gln Asn Leu Ser Pro
    355                 360                 365

Pro Asn Leu Ala Met Lys Ile Ala His Tyr Val Thr Gly Ser Ile His
370                 375                 380

Ser Ile Gly Gly Val His His Gly Ser Tyr Ser Ile Gln Arg Thr Glu
385                 390                 395                 400

Lys Ser Ile Thr Lys Val Asn Leu Val Phe Pro Ile Val Ile Val His
            405                 410                 415

Gly Met Tyr Lys Cys Gln Arg Glu Pro Ser Lys Glu Val Val Trp Ala
        420                 425                 430

Glu Pro Val Thr Gly Ile Leu Phe Lys Ser Pro Ile Pro Thr His Phe
    435                 440                 445

Ser Leu Ser Ser Ser Trp Leu Pro Gly Val Asn Gly Ser Ser Ile Val
450                 455                 460

Pro Leu Thr Gly Gln Ile Leu Leu Pro Glu Ile Thr Met Asp His Leu
465                 470                 475                 480

Glu Val Val Gln Gln Val Glu Ala Lys Met Val Lys Ser Met Tyr Thr
            485                 490                 495

Asn Val Glu Leu Phe Gly Ser Thr Glu Glu Phe Gln Arg Tyr Gln Thr
        500                 505                 510

Gln Gly Ile Thr Ser Asp Glu Gln Ser Asn Thr Val Asn Pro Trp Ile
    515                 520                 525

Gly Leu
530

<210> SEQ ID NO 3
<211> LENGTH: 550
<212> TYPE: PRT
<213> ORGANISM: Artificial Sequence
<220> FEATURE:
<223> OTHER INFORMATION: ectodomain of SFRV glycoprotein variant

<400> SEQUENCE: 3

Met Val Phe Leu Ser Leu Ser Thr Ile Ile Phe Ile Leu Ser Leu Arg
1               5                   10                  15

Ala Val Thr Cys Ser Asn Pro Leu Ser Tyr Pro Asn Gly Ile Leu Thr
            20                  25                  30

Asn Asn Ser Thr His Asn His Pro Leu Ser Asp Phe Tyr Ile Phe Tyr
        35                  40                  45

Glu Asn Ser Ser Leu Thr Tyr Thr Gln Phe Pro Val Ala Pro Asp Cys
    50                  55                  60

Ser Ser Ile Leu Asp Thr Arg Asp Glu Gln Tyr Pro Thr Thr Val Thr
65                  70                  75                  80

Leu Trp Lys Val Asp Gln Glu Ser Gln Ala Glu Trp Gly Leu Leu Leu
            85                  90                  95

Trp Gln Glu Arg Ile Asp Thr Thr Cys Ser Trp Asn Phe Trp Gly Asn
        100                 105                 110

Tyr Lys Gly Ser Ile Val Ser Lys Ser Ser Val Pro Leu Lys Asp Ile
    115                 120                 125
```

```
Pro Ser Gly Ser Ala Arg Asn Gly Tyr Trp Ala Leu Ser Asn Asp Glu
    130                 135                 140

Val Gln Glu Ile Asp His Val Pro Tyr Asn Leu Arg Tyr Tyr Cys Tyr
145                 150                 155                 160

Trp Cys Arg Asn Glu Tyr Pro Gly Ser Phe Tyr Met Arg Tyr Val Lys
                165                 170                 175

Lys Val Arg Ile Ile Arg Asn Pro Asp Gly Ser Ile Lys Thr Pro Arg
                180                 185                 190

Gly Ser Trp Val His Glu Leu Asp Asn Leu Trp Gly Asp Gln Met Arg
        195                 200                 205

Tyr Leu Val Ile Arg Arg Phe Gly Gly Glu Ser Ser Cys Pro Leu Lys
    210                 215                 220

Ile Tyr Asp Val Arg Ala Gly Val Leu Ser Lys Ser Arg Ser Asn Phe
225                 230                 235                 240

Ile Leu Val Ser Leu Pro Ser Leu Asn Leu Gln Phe Ser Val Ser Leu
                245                 250                 255

Glu Ser Thr Glu Thr Lys Cys Ser Phe Gly Asp Lys Tyr Tyr Asp Ile
                260                 265                 270

Val Gln Ser Met Gly Gly Tyr Leu Leu Ser Ile Asp Ile Gly Asn Ala
                275                 280                 285

Asn Trp Arg Gly Pro Trp Asp Pro Thr Pro Gln His Pro Gly Arg Glu
                290                 295                 300

Arg Gln Ser Ile Met Glu Phe Pro Asp Gln Thr Ser Phe Arg Tyr Asn
305                 310                 315                 320

Gln Phe Ile Asn Tyr His Ser Ser Pro Arg His Lys Gln His Asp Gln
                325                 330                 335

Glu Phe Glu Phe Pro Leu Ser Leu Lys Ser Ser Tyr Asp Tyr Ala Gln
                340                 345                 350

Phe Arg Tyr Glu Gln Asn Phe Ile Ile Arg Gln Ile Asn Lys Asn Phe
                355                 360                 365

Gly Leu Leu Gln Lys Ser Ile Cys Asp Ile Gln Phe Ser Lys Trp Gln
        370                 375                 380

Asn Leu Ser Pro Pro Asn Leu Ala Met Lys Ile Ala His Tyr Val Thr
385                 390                 395                 400

Gly Ser Ile His Ser Ile Gly Gly Val His His Gly Ser Tyr Ser Ile
                405                 410                 415

Gln Arg Thr Glu Lys Ser Ile Thr Lys Val Asn Leu Val Phe Pro Ile
                420                 425                 430

Val Ile Val His Gly Met Tyr Lys Cys Gln Arg Glu Pro Ser Lys Glu
        435                 440                 445

Val Val Trp Ala Glu Pro Val Thr Gly Ile Leu Phe Lys Ser Pro Ile
450                 455                 460

Pro Thr His Phe Ser Leu Ser Ser Trp Leu Pro Gly Val Asn Gly
465                 470                 475                 480

Ser Ser Ile Val Pro Leu Thr Gly Gln Ile Leu Leu Pro Glu Ile Thr
                485                 490                 495

Met Asp His Leu Glu Val Val Gln Gln Val Glu Ala Lys Met Val Lys
                500                 505                 510

Ser Met Tyr Thr Asn Val Glu Leu Phe Gly Ser Thr Glu Glu Phe Gln
        515                 520                 525

Arg Tyr Gln Thr Gln Gly Ile Thr Ser Asp Glu Gln Ser Asn Thr Val
        530                 535                 540

Asn Pro Trp Ile Gly Leu
```

```
545             550

<210> SEQ ID NO 4
<211> LENGTH: 610
<212> TYPE: PRT
<213> ORGANISM: Artificial Sequence
<220> FEATURE:
<223> OTHER INFORMATION: SFRV glycoprotein variant

<400> SEQUENCE: 4

Met Val Phe Leu Ser Leu Ser Thr Ile Ile Phe Ile Leu Ser Leu Arg
1               5                   10                  15

Ala Val Thr Cys Ser Asn Pro Leu Ser Tyr Pro Asn Gly Ile Leu Thr
            20                  25                  30

Asn Asn Ser Thr His Asn His Pro Leu Ser Asp Phe Tyr Ile Phe Tyr
        35                  40                  45

Glu Asn Ser Ser Leu Thr Tyr Thr Gln Phe Pro Val Ala Pro Asp Cys
    50                  55                  60

Ser Ser Ile Leu Asp Thr Arg Asp Glu Gln Tyr Pro Thr Thr Val Thr
65                  70                  75                  80

Leu Trp Lys Val Asp Gln Glu Ser Gln Ala Glu Trp Gly Leu Leu Leu
                85                  90                  95

Trp Gln Glu Arg Ile Asp Thr Thr Cys Ser Trp Asn Phe Trp Gly Asn
            100                 105                 110

Tyr Lys Gly Ser Ile Val Ser Lys Ser Val Pro Leu Lys Asp Ile
        115                 120                 125

Pro Ser Gly Ser Ala Arg Asn Gly Tyr Trp Ala Leu Ser Asn Asp Glu
    130                 135                 140

Val Gln Glu Ile Asp His Val Pro Tyr Asn Leu Arg Tyr Tyr Cys Tyr
145                 150                 155                 160

Trp Cys Arg Asn Glu Tyr Pro Gly Ser Phe Tyr Met Arg Tyr Val Lys
                165                 170                 175

Lys Val Arg Ile Ile Arg Asn Pro Asp Gly Ser Ile Lys Thr Pro Arg
            180                 185                 190

Gly Ser Trp Val His Glu Leu Asp Asn Leu Trp Gly Asp Gln Met Arg
        195                 200                 205

Tyr Leu Val Ile Arg Arg Phe Gly Gly Glu Ser Ser Cys Pro Leu Lys
    210                 215                 220

Ile Tyr Asp Val Arg Ala Gly Val Leu Ser Lys Ser Arg Ser Asn Phe
225                 230                 235                 240

Ile Leu Val Ser Leu Pro Ser Leu Asn Leu Gln Phe Ser Val Ser Leu
                245                 250                 255

Glu Ser Thr Glu Thr Lys Cys Ser Phe Gly Asp Lys Thr Tyr Asp Ile
            260                 265                 270

Val Gln Ser Met Gly Gly Tyr Leu Leu Ser Ile Asp Ile Gly Asn Ala
        275                 280                 285

Asn Trp Arg Gly Pro Trp Asp Pro Thr Pro Gln His Pro Gly Arg Glu
    290                 295                 300

Arg Gln Ser Ile Met Glu Phe Pro Asp Gln Thr Ser Phe Arg Tyr Asn
305                 310                 315                 320

Gln Phe Ile Asn Tyr His Ser Ser Pro Arg His Lys Gln His Asp Gln
                325                 330                 335

Glu Phe Glu Phe Pro Leu Ser Leu Lys Ser Ser Tyr Asp Tyr Ala Gln
            340                 345                 350

Phe Arg Tyr Glu Gln Asn Phe Ile Ile Arg Gln Ile Asn Lys Asn Phe
```

```
                355                 360                 365
Gly Leu Leu Gln Lys Ser Ile Cys Asp Ile Gln Phe Ser Lys Trp Gln
            370                 375                 380

Asn Leu Ser Pro Pro Asn Leu Ala Met Lys Ile Ala His Tyr Val Thr
385                 390                 395                 400

Gly Ser Ile His Ser Ile Gly Gly Val His Gly Ser Tyr Ser Ile
                405                 410                 415

Gln Arg Thr Glu Lys Ser Ile Thr Lys Val Asn Leu Val Phe Pro Ile
            420                 425                 430

Val Ile Val His Gly Met Tyr Lys Cys Gln Arg Glu Pro Ser Lys Glu
        435                 440                 445

Val Val Trp Ala Glu Pro Val Thr Gly Ile Leu Phe Lys Ser Pro Ile
        450                 455                 460

Pro Thr His Phe Ser Leu Ser Ser Ser Trp Leu Pro Gly Val Asn Gly
465                 470                 475                 480

Ser Ser Ile Val Pro Leu Thr Gly Gln Ile Leu Leu Pro Glu Ile Thr
                485                 490                 495

Met Asp His Leu Glu Val Val Gln Gln Val Glu Ala Lys Met Val Lys
            500                 505                 510

Ser Met Tyr Thr Asn Val Glu Leu Phe Gly Ser Thr Glu Glu Phe Gln
        515                 520                 525

Arg Tyr Gln Thr Gln Gly Ile Thr Ser Asp Glu Gln Ser Asn Thr Val
        530                 535                 540

Asn Pro Trp Ile Gly Leu Leu Ile His Gly Gly Val Ser Ile Ala Thr
545                 550                 555                 560

Gly Ile Leu Val Ala Leu Leu Ile Pro Ser Ile Leu Lys Leu Phe Arg
                565                 570                 575

His Ile Ile Glu Lys Gly Glu Ala Ser Leu Glu Arg Leu His Leu
            580                 585                 590

Arg Glu Thr Ser Arg Lys Glu Phe Val Lys Val Arg Gly Lys Pro Trp
        595                 600                 605

Gly Val
    610

<210> SEQ ID NO 5
<211> LENGTH: 233
<212> TYPE: PRT
<213> ORGANISM: Cavia porcellus

<400> SEQUENCE: 5

Arg Thr Pro Gln Pro Asn Pro Cys Thr Cys Pro Lys Cys Pro Pro
1               5                   10                  15

Glu Asn Leu Gly Gly Pro Ser Val Phe Ile Phe Pro Lys Pro Lys
            20                  25                  30

Asp Thr Leu Met Ile Ser Leu Thr Pro Arg Val Thr Cys Val Val Val
            35                  40                  45

Asp Val Ser Gln Asp Glu Pro Glu Val Gln Phe Thr Trp Phe Val Asp
        50                  55                  60

Asn Lys Pro Val Gly Asn Ala Glu Thr Lys Pro Arg Val Glu Gln Tyr
65                  70                  75                  80

Asn Thr Thr Phe Arg Val Glu Ser Val Leu Pro Ile Gln His Gln Asp
                85                  90                  95

Trp Leu Arg Gly Lys Glu Phe Lys Cys Lys Val Tyr Asn Lys Ala Leu
            100                 105                 110
```

Pro Ala Pro Ile Glu Lys Thr Ile Ser Lys Thr Lys Gly Ala Pro Arg
            115                 120                 125

Met Pro Asp Val Tyr Thr Leu Pro Pro Ser Arg Asp Glu Leu Ser Lys
130                 135                 140

Ser Lys Val Ser Val Thr Cys Leu Ile Ile Asn Phe Phe Pro Ala Asp
145                 150                 155                 160

Ile His Val Glu Trp Ala Ser Asn Arg Val Pro Val Ser Glu Lys Glu
                    165                 170                 175

Tyr Lys Asn Thr Pro Pro Ile Glu Asp Ala Asp Gly Ser Tyr Phe Leu
            180                 185                 190

Tyr Ser Lys Leu Thr Val Asp Lys Ser Ala Trp Asp Gln Gly Thr Val
        195                 200                 205

Tyr Thr Cys Ser Val Met His Glu Ala Leu His Asn His Val Thr Gln
    210                 215                 220

Lys Ala Ile Ser Arg Ser Pro Gly Lys
225                 230

<210> SEQ ID NO 6
<211> LENGTH: 229
<212> TYPE: PRT
<213> ORGANISM: Sus scrofa

<400> SEQUENCE: 6

Thr Lys Thr Lys Pro Pro Cys Pro Ile Cys Pro Ala Cys Glu Ser Pro
1               5                   10                  15

Gly Pro Ser Val Phe Ile Phe Pro Pro Lys Pro Lys Asp Thr Leu Met
            20                  25                  30

Ile Ser Arg Thr Pro Gln Val Thr Cys Val Val Val Asp Val Ser Gln
        35                  40                  45

Glu Asn Pro Glu Val Gln Phe Ser Trp Tyr Val Asp Gly Val Glu Val
    50                  55                  60

His Thr Ala Gln Thr Arg Pro Lys Glu Gln Phe Asn Ser Thr Tyr
65                  70                  75                  80

Arg Val Val Ser Val Leu Pro Ile Gln His Gln Asp Trp Leu Asn Gly
                85                  90                  95

Lys Glu Phe Lys Cys Lys Val Asn Asn Lys Asp Leu Pro Ala Pro Ile
            100                 105                 110

Thr Arg Ile Ile Ser Lys Ala Lys Gly Gln Thr Arg Glu Pro Gln Val
        115                 120                 125

Tyr Thr Leu Pro Pro His Ala Glu Glu Leu Ser Arg Ser Lys Val Ser
    130                 135                 140

Ile Thr Cys Leu Val Ile Gly Phe Tyr Pro Pro Asp Ile Asp Val Glu
145                 150                 155                 160

Trp Gln Arg Asn Gly Gln Pro Glu Pro Glu Gly Asn Tyr Arg Thr Thr
                165                 170                 175

Pro Pro Gln Gln Asp Val Asp Gly Thr Tyr Phe Leu Tyr Ser Lys Phe
            180                 185                 190

Ser Val Asp Lys Ala Ser Trp Gln Gly Gly Gly Ile Phe Gln Cys Ala
        195                 200                 205

Val Met His Glu Ala Leu His Asn His Tyr Thr Gln Lys Ser Ile Ser
    210                 215                 220

Lys Thr Pro Gly Lys
225

<210> SEQ ID NO 7

```
<211> LENGTH: 32
<212> TYPE: PRT
<213> ORGANISM: Saccharomyces cerevisiae

<400> SEQUENCE: 7

Met Lys Gln Leu Glu Asp Lys Val Glu Leu Leu Ser Lys Asn Tyr
1               5                   10                  15

His Leu Glu Asn Glu Val Ala Arg Leu Lys Lys Leu Val Gly Glu Arg
            20                  25                  30

<210> SEQ ID NO 8
<211> LENGTH: 27
<212> TYPE: PRT
<213> ORGANISM: Escherichia virus T4

<400> SEQUENCE: 8

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 9
<211> LENGTH: 11
<212> TYPE: PRT
<213> ORGANISM: Artificial Sequence
<220> FEATURE:
<223> OTHER INFORMATION: linker

<400> SEQUENCE: 9

Gly Gly Glu Asn Leu Tyr Phe Gln Gly Gly Ser
1               5                   10

<210> SEQ ID NO 10
<211> LENGTH: 3
<212> TYPE: PRT
<213> ORGANISM: Artificial Sequence
<220> FEATURE:
<223> OTHER INFORMATION: linker

<400> SEQUENCE: 10

Gly Gly Ser
1

<210> SEQ ID NO 11
<211> LENGTH: 10
<212> TYPE: PRT
<213> ORGANISM: Artificial Sequence
<220> FEATURE:
<223> OTHER INFORMATION: linker

<400> SEQUENCE: 11

Ala Ser Gly Gly Gly Gly Gly Gly Gly Gly
1               5                   10

<210> SEQ ID NO 12
<211> LENGTH: 773
<212> TYPE: PRT
<213> ORGANISM: Artificial Sequence
<220> FEATURE:
<223> OTHER INFORMATION: fusion protein

<400> SEQUENCE: 12

Asn Pro Leu Ser Tyr Pro Asn Gly Ile Leu Thr Asn Asn Ser Thr His
1               5                   10                  15

Asn His Pro Leu Ser Asp Phe Tyr Ile Phe Tyr Glu Asn Ser Ser Leu
```

```
            20                  25                  30
Thr Tyr Thr Gln Phe Pro Val Ala Pro Asp Cys Ser Ser Ile Leu Asp
        35                  40                  45
Thr Arg Asp Glu Gln Tyr Pro Thr Val Thr Leu Trp Lys Val Asp
50                  55                  60
Gln Glu Ser Gln Ala Glu Trp Gly Leu Leu Leu Trp Gln Glu Arg Ile
65                  70                  75                  80
Asp Thr Thr Cys Ser Trp Asn Phe Trp Gly Asn Tyr Lys Gly Ser Ile
                85                  90                  95
Val Ser Lys Ser Ser Val Pro Leu Lys Asp Ile Pro Ser Gly Ser Ala
            100                 105                 110
Arg Asn Gly Tyr Trp Ala Leu Ser Asn Asp Glu Val Gln Glu Ile Asp
        115                 120                 125
His Val Pro Tyr Asn Leu Arg Tyr Tyr Cys Tyr Trp Cys Arg Asn Glu
    130                 135                 140
Tyr Pro Gly Ser Phe Tyr Met Arg Tyr Val Lys Lys Val Arg Ile Ile
145                 150                 155                 160
Arg Asn Pro Asp Gly Ser Ile Lys Thr Pro Arg Gly Ser Trp Val His
                165                 170                 175
Glu Leu Asp Asn Leu Trp Gly Asp Gln Met Arg Tyr Leu Val Ile Arg
            180                 185                 190
Arg Phe Gly Gly Glu Ser Ser Cys Pro Leu Lys Ile Tyr Asp Val Arg
        195                 200                 205
Ala Gly Val Leu Ser Lys Ser Arg Ser Asn Phe Ile Leu Val Ser Leu
    210                 215                 220
Pro Ser Leu Asn Leu Gln Phe Ser Val Ser Leu Glu Ser Thr Glu Thr
225                 230                 235                 240
Lys Cys Ser Phe Gly Asp Lys Thr Tyr Asp Ile Val Gln Ser Met Gly
                245                 250                 255
Gly Tyr Leu Leu Ser Ile Asp Ile Gly Asn Ala Asn Trp Arg Gly Pro
            260                 265                 270
Trp Asp Pro Thr Pro Gln His Pro Gly Arg Glu Arg Gln Ser Ile Met
        275                 280                 285
Glu Phe Pro Asp Gln Thr Ser Phe Arg Tyr Asn Gln Phe Ile Asn Tyr
    290                 295                 300
His Ser Ser Pro Arg His Lys Gln His Asp Gln Glu Phe Glu Phe Pro
305                 310                 315                 320
Leu Ser Leu Lys Ser Ser Tyr Asp Tyr Ala Gln Phe Arg Tyr Glu Gln
                325                 330                 335
Asn Phe Ile Ile Arg Gln Ile Asn Lys Asn Phe Gly Leu Leu Gln Lys
            340                 345                 350
Ser Ile Cys Asp Ile Gln Phe Ser Lys Trp Gln Asn Leu Ser Pro Pro
        355                 360                 365
Asn Leu Ala Met Lys Ile Ala His Tyr Val Thr Gly Ser Ile His Ser
    370                 375                 380
Ile Gly Gly Val His His Gly Ser Tyr Ser Ile Gln Arg Thr Glu Lys
385                 390                 395                 400
Ser Ile Thr Lys Val Asn Leu Val Phe Pro Ile Val Ile His Gly
                405                 410                 415
Met Tyr Lys Cys Gln Arg Glu Pro Ser Lys Glu Val Val Trp Ala Glu
            420                 425                 430
Pro Val Thr Gly Ile Leu Phe Lys Ser Pro Ile Pro Thr His Phe Ser
        435                 440                 445
```

-continued

Leu Ser Ser Ser Trp Leu Pro Gly Val Asn Gly Ser Ser Ile Val Pro
    450                 455                 460

Leu Thr Gly Gln Ile Leu Leu Pro Glu Ile Thr Met Asp His Leu Glu
465                 470                 475                 480

Val Val Gln Gln Val Glu Ala Lys Met Val Lys Ser Met Tyr Thr Asn
                485                 490                 495

Val Glu Leu Phe Gly Ser Thr Glu Phe Gln Arg Tyr Gln Thr Gln
            500                 505                 510

Gly Ile Thr Ser Asp Glu Gln Ser Asn Thr Val Asn Pro Trp Ile Gly
        515                 520                 525

Leu Gly Gly Glu Asn Leu Tyr Phe Gln Gly Gly Ser Arg Thr Pro Gln
    530                 535                 540

Pro Asn Pro Cys Thr Cys Pro Lys Cys Pro Pro Glu Asn Leu Gly
545                 550                 555                 560

Gly Pro Ser Val Phe Ile Phe Pro Pro Lys Pro Lys Asp Thr Leu Met
                565                 570                 575

Ile Ser Leu Thr Pro Arg Val Thr Cys Val Val Asp Val Ser Gln
            580                 585                 590

Asp Glu Pro Glu Val Gln Phe Thr Trp Phe Val Asp Asn Lys Pro Val
        595                 600                 605

Gly Asn Ala Glu Thr Lys Pro Arg Val Glu Gln Tyr Asn Thr Thr Phe
    610                 615                 620

Arg Val Glu Ser Val Leu Pro Ile Gln His Gln Asp Trp Leu Arg Gly
625                 630                 635                 640

Lys Glu Phe Lys Cys Lys Val Tyr Asn Lys Ala Leu Pro Ala Pro Ile
                645                 650                 655

Glu Lys Thr Ile Ser Lys Thr Lys Gly Ala Pro Arg Met Pro Asp Val
            660                 665                 670

Tyr Thr Leu Pro Pro Ser Arg Asp Glu Leu Ser Lys Ser Lys Val Ser
        675                 680                 685

Val Thr Cys Leu Ile Ile Asn Phe Phe Pro Ala Asp Ile His Val Glu
    690                 695                 700

Trp Ala Ser Asn Arg Val Pro Val Ser Glu Lys Glu Tyr Lys Asn Thr
705                 710                 715                 720

Pro Pro Ile Glu Asp Ala Asp Gly Ser Tyr Phe Leu Tyr Ser Lys Leu
                725                 730                 735

Thr Val Asp Lys Ser Ala Trp Asp Gln Gly Thr Val Tyr Thr Cys Ser
            740                 745                 750

Val Met His Glu Ala Leu His Asn His Val Thr Gln Lys Ala Ile Ser
        755                 760                 765

Arg Ser Pro Gly Lys
    770

<210> SEQ ID NO 13
<211> LENGTH: 564
<212> TYPE: PRT
<213> ORGANISM: Artificial Sequence
<220> FEATURE:
<223> OTHER INFORMATION: fusion protein

<400> SEQUENCE: 13

Asn Pro Leu Ser Tyr Pro Asn Gly Ile Leu Thr Asn Asn Ser Thr His
1               5                   10                  15

Asn His Pro Leu Ser Asp Phe Tyr Ile Phe Tyr Glu Asn Ser Ser Leu
            20                  25                  30

```
Thr Tyr Thr Gln Phe Pro Val Ala Pro Asp Cys Ser Ser Ile Leu Asp
        35                  40                  45

Thr Arg Asp Glu Gln Tyr Pro Thr Thr Val Thr Leu Trp Lys Val Asp
 50                  55                  60

Gln Glu Ser Gln Ala Glu Trp Gly Leu Leu Trp Gln Glu Arg Ile
 65                  70                  75                  80

Asp Thr Thr Cys Ser Trp Asn Phe Trp Gly Asn Tyr Lys Gly Ser Ile
                 85                  90                  95

Val Ser Lys Ser Ser Val Pro Leu Lys Asp Ile Pro Ser Gly Ser Ala
                100                 105                 110

Arg Asn Gly Tyr Trp Ala Leu Ser Asn Asp Glu Val Gln Glu Ile Asp
                115                 120                 125

His Val Pro Tyr Asn Leu Arg Tyr Tyr Cys Tyr Trp Cys Arg Asn Glu
        130                 135                 140

Tyr Pro Gly Ser Phe Tyr Met Arg Tyr Val Lys Lys Val Arg Ile Ile
145                 150                 155                 160

Arg Asn Pro Asp Gly Ser Ile Lys Thr Pro Arg Gly Ser Trp Val His
                165                 170                 175

Glu Leu Asp Asn Leu Trp Gly Asp Gln Met Arg Tyr Leu Val Ile Arg
                180                 185                 190

Arg Phe Gly Gly Glu Ser Ser Cys Pro Leu Lys Ile Tyr Asp Val Arg
        195                 200                 205

Ala Gly Val Leu Ser Lys Ser Arg Ser Asn Phe Ile Leu Val Ser Leu
        210                 215                 220

Pro Ser Leu Asn Leu Gln Phe Ser Val Ser Leu Glu Ser Thr Glu Thr
225                 230                 235                 240

Lys Cys Ser Phe Gly Asp Lys Thr Tyr Asp Ile Val Gln Ser Met Gly
                245                 250                 255

Gly Tyr Leu Leu Ser Ile Asp Ile Gly Asn Ala Asn Trp Arg Gly Pro
                260                 265                 270

Trp Asp Pro Thr Pro Gln His Pro Gly Arg Glu Arg Gln Ser Ile Met
        275                 280                 285

Glu Phe Pro Asp Gln Thr Ser Phe Arg Tyr Asn Gln Phe Ile Asn Tyr
        290                 295                 300

His Ser Ser Pro Arg His Lys Gln His Asp Gln Glu Phe Glu Phe Pro
305                 310                 315                 320

Leu Ser Leu Lys Ser Ser Tyr Asp Tyr Ala Gln Phe Arg Tyr Glu Gln
                325                 330                 335

Asn Phe Ile Ile Arg Gln Ile Asn Lys Asn Phe Gly Leu Leu Gln Lys
                340                 345                 350

Ser Ile Cys Asp Ile Gln Phe Ser Lys Trp Gln Asn Leu Ser Pro Pro
        355                 360                 365

Asn Leu Ala Met Lys Ile Ala His Tyr Val Thr Gly Ser Ile His Ser
        370                 375                 380

Ile Gly Gly Val His His Gly Ser Tyr Ser Ile Gln Arg Thr Glu Lys
385                 390                 395                 400

Ser Ile Thr Lys Val Asn Leu Val Phe Pro Ile Val Ile Val His Gly
                405                 410                 415

Met Tyr Lys Cys Gln Arg Glu Pro Ser Lys Glu Val Val Trp Ala Glu
                420                 425                 430

Pro Val Thr Gly Ile Leu Phe Lys Ser Pro Ile Pro Thr His Phe Ser
        435                 440                 445
```

-continued

```
Leu Ser Ser Trp Leu Pro Gly Val Asn Gly Ser Ser Ile Val Pro
450                 455                 460

Leu Thr Gly Gln Ile Leu Leu Pro Glu Ile Thr Met Asp His Leu Glu
465                 470                 475                 480

Val Val Gln Gln Val Glu Ala Lys Met Val Lys Ser Met Tyr Thr Asn
                485                 490                 495

Val Glu Leu Phe Gly Ser Thr Glu Glu Phe Gln Arg Tyr Gln Thr Gln
                500                 505                 510

Gly Ile Thr Ser Asp Glu Gln Ser Asn Thr Val Asn Pro Trp Ile Gly
                515                 520                 525

Leu Gly Gly Ser Met Lys Gln Leu Glu Asp Lys Val Glu Glu Leu Leu
530                 535                 540

Ser Lys Asn Tyr His Leu Glu Asn Glu Val Ala Arg Leu Lys Lys Leu
545                 550                 555                 560

Val Gly Glu Arg

<210> SEQ ID NO 14
<211> LENGTH: 566
<212> TYPE: PRT
<213> ORGANISM: Artificial Sequence
<220> FEATURE:
<223> OTHER INFORMATION: fusion protein

<400> SEQUENCE: 14

Asn Pro Leu Ser Tyr Pro Asn Gly Ile Leu Thr Asn Asn Ser Thr His
1               5                   10                  15

Asn His Pro Leu Ser Asp Phe Tyr Ile Phe Tyr Glu Asn Ser Ser Leu
                20                  25                  30

Thr Tyr Thr Gln Phe Pro Val Ala Pro Asp Cys Ser Ser Ile Leu Asp
            35                  40                  45

Thr Arg Asp Glu Gln Tyr Pro Thr Thr Val Thr Leu Trp Lys Val Asp
    50                  55                  60

Gln Glu Ser Gln Ala Glu Trp Gly Leu Leu Leu Trp Gln Glu Arg Ile
65                  70                  75                  80

Asp Thr Thr Cys Ser Trp Asn Phe Trp Gly Asn Tyr Lys Gly Ser Ile
                85                  90                  95

Val Ser Lys Ser Ser Val Pro Leu Lys Asp Ile Pro Ser Gly Ser Ala
                100                 105                 110

Arg Asn Gly Tyr Trp Ala Leu Ser Asn Asp Glu Val Gln Glu Ile Asp
            115                 120                 125

His Val Pro Tyr Asn Leu Arg Tyr Tyr Cys Tyr Trp Cys Arg Asn Glu
    130                 135                 140

Tyr Pro Gly Ser Phe Tyr Met Arg Tyr Val Lys Lys Val Arg Ile Ile
145                 150                 155                 160

Arg Asn Pro Asp Gly Ser Ile Lys Thr Pro Arg Gly Ser Trp Val His
                165                 170                 175

Glu Leu Asp Asn Leu Trp Gly Asp Gln Met Arg Tyr Leu Val Ile Arg
                180                 185                 190

Arg Phe Gly Gly Glu Ser Ser Cys Pro Leu Lys Ile Tyr Asp Val Arg
            195                 200                 205

Ala Gly Val Leu Ser Lys Ser Arg Ser Asn Phe Ile Leu Val Ser Leu
    210                 215                 220

Pro Ser Leu Asn Leu Gln Phe Ser Val Ser Leu Glu Ser Thr Glu Thr
225                 230                 235                 240

Lys Cys Ser Phe Gly Asp Lys Thr Tyr Asp Ile Val Gln Ser Met Gly
```

-continued

```
                245                 250                 255
Gly Tyr Leu Leu Ser Ile Asp Ile Gly Asn Ala Asn Trp Arg Gly Pro
            260                 265                 270

Trp Asp Pro Thr Pro Gln His Pro Gly Arg Glu Arg Gln Ser Ile Met
        275                 280                 285

Glu Phe Pro Asp Gln Thr Ser Phe Arg Tyr Asn Gln Phe Ile Asn Tyr
    290                 295                 300

His Ser Ser Pro Arg His Lys Gln His Asp Gln Glu Phe Glu Phe Pro
305                 310                 315                 320

Leu Ser Leu Lys Ser Ser Tyr Asp Tyr Ala Gln Phe Arg Tyr Glu Gln
                325                 330                 335

Asn Phe Ile Ile Arg Gln Ile Asn Lys Asn Phe Gly Leu Leu Gln Lys
            340                 345                 350

Ser Ile Cys Asp Ile Gln Phe Ser Lys Trp Gln Asn Leu Ser Pro Pro
        355                 360                 365

Asn Leu Ala Met Lys Ile Ala His Tyr Val Thr Gly Ser Ile His Ser
    370                 375                 380

Ile Gly Gly Val His His Gly Ser Tyr Ser Ile Gln Arg Thr Glu Lys
385                 390                 395                 400

Ser Ile Thr Lys Val Asn Leu Val Phe Pro Ile Val Ile Val His Gly
                405                 410                 415

Met Tyr Lys Cys Gln Arg Glu Pro Ser Lys Glu Val Val Trp Ala Glu
            420                 425                 430

Pro Val Thr Gly Ile Leu Phe Lys Ser Pro Ile Pro Thr His Phe Ser
        435                 440                 445

Leu Ser Ser Ser Trp Leu Pro Gly Val Asn Gly Ser Ser Ile Val Pro
    450                 455                 460

Leu Thr Gly Gln Ile Leu Leu Pro Glu Ile Thr Met Asp His Leu Glu
465                 470                 475                 480

Val Val Gln Gln Val Glu Ala Lys Met Val Lys Ser Met Tyr Thr Asn
                485                 490                 495

Val Glu Leu Phe Gly Ser Thr Glu Gln Phe Gln Arg Tyr Gln Thr Gln
            500                 505                 510

Gly Ile Thr Ser Asp Glu Gln Ser Asn Thr Val Asn Pro Trp Ile Gly
        515                 520                 525

Leu Ala Ser Gly Gly Gly Gly Gly Gly Tyr Ile Pro Glu
    530                 535                 540

Ala Pro Arg Asp Gly Gln Ala Tyr Val Arg Lys Asp Gly Glu Trp Val
545                 550                 555                 560

Leu Leu Ser Thr Phe Leu
                565
```

<210> SEQ ID NO 15
<211> LENGTH: 550
<212> TYPE: PRT
<213> ORGANISM: SFRV

<400> SEQUENCE: 15

```
Met Val Phe Leu Ser Leu Ser Thr Ile Ile Phe Ile Leu Ser Leu Arg
1               5                   10                  15

Ala Val Thr Cys Ser Asn Pro Leu Ser Tyr Pro Asn Gly Ile Leu Thr
            20                  25                  30

Asn Asn Ser Thr His Asn His Pro Leu Ser Asp Phe Tyr Ile Phe Tyr
        35                  40                  45
```

```
Glu Asn Ser Ser Leu Thr Tyr Thr Gln Phe Pro Val Ala Pro Asp Cys
 50                  55                  60

Ser Ser Ile Leu Asp Thr Arg Asp Glu Gln Tyr Pro Thr Thr Val Thr
 65                  70                  75                  80

Leu Trp Lys Val Asp Gln Glu Ser Gln Ala Glu Trp Gly Leu Leu Leu
                 85                  90                  95

Trp Gln Glu Arg Ile Asp Thr Thr Cys Ser Trp Asn Phe Trp Gly Asn
            100                 105                 110

Tyr Lys Gly Ser Ile Val Ser Lys Ser Ser Val Pro Leu Lys Asp Ile
            115                 120                 125

Pro Ser Gly Ser Ala Arg Asn Gly Tyr Trp Ala Leu Ser Asn Asp Glu
130                 135                 140

Val Gln Glu Ile Asp His Val Pro Tyr Asn Leu Arg Tyr Tyr Cys Tyr
145                 150                 155                 160

Trp Cys Arg Asn Glu Tyr Pro Gly Ser Phe Tyr Met Arg Tyr Val Lys
                165                 170                 175

Lys Val Arg Ile Ile Arg Asn Pro Asp Gly Ser Ile Lys Thr Pro Arg
            180                 185                 190

Gly Ser Trp Val His Glu Leu Asp Asn Leu Trp Gly Asp Gln Met Arg
            195                 200                 205

Tyr Leu Val Ile Arg Arg Phe Gly Glu Ser Ser Cys Pro Leu Lys
210                 215                 220

Ile Tyr Asp Val Arg Ala Gly Val Leu Ser Lys Ser Arg Ser Asn Phe
225                 230                 235                 240

Ile Leu Val Ser Leu Pro Ser Leu Asn Leu Gln Phe Ser Val Ser Leu
                245                 250                 255

Glu Ser Thr Glu Thr Lys Cys Ser Phe Gly Asp Lys Thr Tyr Asp Ile
            260                 265                 270

Val Gln Ser Met Gly Gly Tyr Leu Leu Ser Ile Asp Ile Gly Asn Ala
            275                 280                 285

Asn Trp Arg Gly Pro Trp Asp Pro Thr Pro Gln His Pro Gly Arg Glu
290                 295                 300

Arg Arg Ser Ile Met Glu Phe Pro Asp Gln Thr Ser Phe Arg Tyr Asn
305                 310                 315                 320

Gln Phe Ile Asn Tyr His Ser Ser Pro Arg His Lys Arg His Asp Gln
                325                 330                 335

Glu Phe Glu Phe Pro Leu Ser Leu Lys Ser Ser Tyr Asp Tyr Ala Gln
            340                 345                 350

Phe Arg Tyr Glu Gln Asn Phe Ile Ile Arg Gln Ile Asn Lys Asn Phe
            355                 360                 365

Gly Leu Leu Gln Lys Ser Ile Cys Asp Ile Gln Phe Ser Lys Trp Gln
370                 375                 380

Asn Leu Ser Pro Pro Asn Leu Ala Met Lys Ile Ala His Tyr Val Thr
385                 390                 395                 400

Gly Ser Ile His Ser Ile Gly Gly Val His His Gly Ser Tyr Ser Ile
                405                 410                 415

Gln Arg Thr Glu Lys Ser Ile Thr Lys Val Asn Leu Val Phe Pro Ile
            420                 425                 430

Val Ile Val His Gly Met Tyr Lys Cys Gln Arg Glu Pro Ser Lys Glu
            435                 440                 445

Val Val Trp Ala Glu Pro Val Thr Gly Ile Leu Phe Lys Ser Pro Ile
450                 455                 460

Pro Thr His Phe Ser Leu Ser Ser Ser Trp Leu Pro Gly Val Asn Gly
```

```
                465                 470                 475                 480
Ser Ser Ile Val Pro Leu Thr Gly Gln Ile Leu Leu Pro Glu Ile Thr
                    485                 490                 495

Met Asp His Leu Glu Val Val Gln Gln Val Glu Ala Lys Met Val Lys
                500                 505                 510

Ser Met Tyr Thr Asn Val Glu Leu Phe Gly Ser Thr Glu Glu Phe Gln
                515                 520                 525

Arg Tyr Gln Thr Gln Gly Ile Thr Ser Asp Glu Gln Ser Asn Thr Val
                530                 535                 540

Asn Pro Trp Ile Gly Leu
545                 550

<210> SEQ ID NO 16
<211> LENGTH: 610
<212> TYPE: PRT
<213> ORGANISM: SFRV

<400> SEQUENCE: 16

Met Val Phe Leu Ser Leu Ser Thr Ile Ile Phe Ile Leu Ser Leu Arg
1               5                   10                  15

Ala Val Thr Cys Ser Asn Pro Leu Ser Tyr Pro Asn Gly Ile Leu Thr
                20                  25                  30

Asn Asn Ser Thr His Asn His Pro Leu Ser Asp Phe Tyr Ile Phe Tyr
            35                  40                  45

Glu Asn Ser Ser Leu Thr Tyr Thr Gln Phe Pro Val Ala Pro Asp Cys
    50                  55                  60

Ser Ser Ile Leu Asp Thr Arg Asp Glu Gln Tyr Pro Thr Thr Val Thr
65                  70                  75                  80

Leu Trp Lys Val Asp Gln Glu Ser Gln Ala Glu Trp Gly Leu Leu Leu
                85                  90                  95

Trp Gln Glu Arg Ile Asp Thr Thr Cys Ser Trp Asn Phe Trp Gly Asn
                100                 105                 110

Tyr Lys Gly Ser Ile Val Ser Lys Ser Ser Val Pro Leu Lys Asp Ile
            115                 120                 125

Pro Ser Gly Ser Ala Arg Asn Gly Tyr Trp Ala Leu Ser Asn Asp Glu
    130                 135                 140

Val Gln Glu Ile Asp His Val Pro Tyr Asn Leu Arg Tyr Tyr Cys Tyr
145                 150                 155                 160

Trp Cys Arg Asn Glu Tyr Pro Gly Ser Phe Tyr Met Arg Tyr Val Lys
                165                 170                 175

Lys Val Arg Ile Ile Arg Asn Pro Asp Gly Ser Ile Lys Thr Pro Arg
                180                 185                 190

Gly Ser Trp Val His Glu Leu Asp Asn Leu Trp Gly Asp Gln Met Arg
            195                 200                 205

Tyr Leu Val Ile Arg Arg Phe Gly Gly Glu Ser Ser Cys Pro Leu Lys
    210                 215                 220

Ile Tyr Asp Val Arg Ala Gly Val Leu Ser Lys Ser Arg Ser Asn Phe
225                 230                 235                 240

Ile Leu Val Ser Leu Pro Ser Leu Asn Leu Gln Phe Ser Val Ser Leu
                245                 250                 255

Glu Ser Thr Glu Thr Lys Cys Ser Phe Gly Asp Lys Thr Tyr Asp Ile
                260                 265                 270

Val Gln Ser Met Gly Gly Tyr Leu Leu Ser Ile Asp Ile Gly Asn Ala
            275                 280                 285
```

```
Asn Trp Arg Gly Pro Trp Asp Pro Thr Pro Gln His Pro Gly Arg Glu
    290                 295                 300
Arg Arg Ser Ile Met Glu Phe Pro Asp Gln Thr Ser Phe Arg Tyr Asn
305                 310                 315                 320
Gln Phe Ile Asn Tyr His Ser Ser Pro Arg His Lys Arg His Asp Gln
                325                 330                 335
Glu Phe Glu Phe Pro Leu Ser Leu Lys Ser Ser Tyr Asp Tyr Ala Gln
340                 345                 350
Phe Arg Tyr Glu Gln Asn Phe Ile Ile Arg Gln Ile Asn Lys Asn Phe
            355                 360                 365
Gly Leu Leu Gln Lys Ser Ile Cys Asp Ile Gln Phe Ser Lys Trp Gln
370                 375                 380
Asn Leu Ser Pro Pro Asn Leu Ala Met Lys Ile Ala His Tyr Val Thr
385                 390                 395                 400
Gly Ser Ile His Ser Ile Gly Gly Val His His Gly Ser Tyr Ser Ile
                405                 410                 415
Gln Arg Thr Glu Lys Ser Ile Thr Lys Val Asn Leu Val Phe Pro Ile
            420                 425                 430
Val Ile Val His Gly Met Tyr Lys Cys Gln Arg Glu Pro Ser Lys Glu
435                 440                 445
Val Val Trp Ala Glu Pro Val Thr Gly Ile Leu Phe Lys Ser Pro Ile
450                 455                 460
Pro Thr His Phe Ser Leu Ser Ser Ser Trp Leu Pro Gly Val Asn Gly
465                 470                 475                 480
Ser Ser Ile Val Pro Leu Thr Gly Gln Ile Leu Leu Pro Glu Ile Thr
                485                 490                 495
Met Asp His Leu Glu Val Val Gln Gln Val Glu Ala Lys Met Val Lys
            500                 505                 510
Ser Met Tyr Thr Asn Val Glu Leu Phe Gly Ser Thr Glu Glu Phe Gln
            515                 520                 525
Arg Tyr Gln Thr Gln Gly Ile Thr Ser Asp Glu Gln Ser Asn Thr Val
530                 535                 540
Asn Pro Trp Ile Gly Leu Leu Ile His Gly Gly Val Ser Ile Ala Thr
545                 550                 555                 560
Gly Ile Leu Val Ala Leu Leu Ile Pro Ser Ile Leu Lys Leu Phe Arg
                565                 570                 575
His Ile Ile Glu Lys Gly Glu Ala Ser Leu Glu Glu Arg Leu His Leu
            580                 585                 590
Arg Glu Thr Ser Arg Lys Glu Phe Val Lys Val Arg Gly Lys Pro Trp
            595                 600                 605
Gly Val
    610

<210> SEQ ID NO 17
<211> LENGTH: 2385
<212> TYPE: DNA
<213> ORGANISM: Artificial Sequence
<220> FEATURE:
<223> OTHER INFORMATION: encodes a fusion protein

<400> SEQUENCE: 17
atggttttct taagtttatc aacgatcata tttatcctaa gcctccgggc tgtaacctgc      60
tccaatcctc tctcctatcc taatggcatt ttgactaaca actctactca caatcatccc     120
ctatcggact tttatatttt ttatgagaac agttccctta cctatactca attccctgtg     180
```

```
gccccagact gctctagtat tctagatact agagatgagc agtatcccac cactgttact    240
ttgtggaagg ttgatcaaga atctcaagct gagtggggac tccttttatg gcaagagaga    300
attgacacca cttgctcctg gaacttctgg ggcaattaca aaggatccat tgtatctaaa    360
tcctcagtac ctctaaagga tatcccatcg ggtagtgccc ggaatggata ttgggctttg    420
agcaatgatg aagttcaaga gattgatcat gtcccttaca acttgagata ttattgttac    480
tggtgcagaa atgaatatcc tgggagcttt tatatgagat atgtaaagaa agttcggatc    540
ataagaaatc ctgatgggtc tataaagact cctagaggat cctgggttca tgagttggac    600
aacttgtggg gagatcagat gaggtatcta gttattcgaa gatttggggg agaatctagc    660
tgccctctta agatatatga tgtgagagca ggggttctgt caaaatctcg gtcaaacttc    720
atcttagtgt cccttccctc cttgaatttg cagttctctg tatcacttga atccactgag    780
acgaaatgct catttggaga taagacatat gatattgtgc agagcatggg aggctatctc    840
ctctccatcg acataggtaa tgcgaactgg cgaggccctt gggatcctac ccctcagcat    900
ccgggtcgtg aaagacagtc aattatggag tttccggatc aaacatcttt cagatataac    960
caatttataa attatcactc atccccaaga cacaagcagc atgatcaaga atttgagttc   1020
cctctcagtc taaaatccag ttatgattat gctcaattta gatatgagca gaatttcatc   1080
atccgacaga tcaataagaa ttttggatta ttacagaaga gcatttgtga tattcagttt   1140
tctaagtggc agaatctcag tccacccaat cttgctatga aaattgctca ttatgtcacc   1200
ggctctatcc actctatagg tggtgttcat catggatctt attcaattca agaacggaa    1260
aaatccatta ctaaggtcaa tctggtgttt cccattgtta ttgttcatgg aatgtataag   1320
tgccaaaggg aaccatccaa ggaggtggtt tgggcagaac ccgtcacagg gatcttattc   1380
aagtctccta ttccgactca tttctcacta agttcctctt ggctacctgg ggtaaatggt   1440
tcttctattg tccctctgac aggtcaaatt cttctccctg aaatcacaat ggatcacttg   1500
gaggttgtac aacaggttga agcaaagatg gtcaaaagta tgtacacgaa tgtagagttg   1560
tttggatcaa cagaggaatt tcaaagatac caaactcagg gaattacctc tgatgaacaa   1620
tcaaatacag taaatccttg gattgggctt ggaggtgaaa acctgtattt tcagggcggc   1680
tcgcgaactc ctcaacccaa cccgtgtaca tgtcccaagt gcccacctcc tgaaaacctg   1740
ggtggaccat ctgtcttcat cttttccccg aagcccaagg acacgctcat gatctccctg   1800
accccctaggg tcacatgtgt ggtggtagat gtgagccaag atgagcctga agtccagttc   1860
acatggttcg tggacaacaa accggtcggc aatgctgaga caaagccccg agtggagcaa   1920
tacaacacga cattccgcgt ggaaagtgtc ctccccatcc agcaccagga ctggctgagg   1980
ggcaaggaat tcaagtgcaa ggtctacaac aaagccctgc cagcccccat agagaagacc   2040
atctccaaaa ccaaggggc tccccgcatg ccagatgtgt acacccttcc cccgtcccga    2100
gacgagctat ccaagagcaa agtcagtgtg acctgcctga tcatcaactt ctttcctgcc   2160
gacatccacg tggagtgggc cagcaatagg gttccagtga gtgagaagga atacaagaac   2220
accccacccca ttgaggacgc tgacgggtcc tacttcctct acagcaagct cactgtggat   2280
aagagcgcgt gggatcaggg aaccgtctac acctgctccg tgatgcatga agccctgcac   2340
aatcatgtca ctcagaaggc catctcccgc tctccgggta aatga                   2385
```

<210> SEQ ID NO 18
<211> LENGTH: 1758
<212> TYPE: DNA
<213> ORGANISM: Artificial Sequence
<220> FEATURE:
<223> OTHER INFORMATION: encodes a fusion protein

<400> SEQUENCE: 18

| | | |
|---|---|---|
| atggttttct taagtttatc aacgatcata tttatcctaa gcctccgggc tgtaacctgc | 60 |
| tccaatcctc tctcctatcc taatggcatt ttgactaaca actctactca caatcatccc | 120 |
| ctatcggact tttatatttt ttatgagaac agttccctta cctatactca attccctgtg | 180 |
| gccccagact gctctagtat tctagatact agagatgagc agtatcccac cactgttact | 240 |
| ttgtggaagg ttgatcaaga atctcaagct gagtggggac tccttttatg gcaagagaga | 300 |
| attgacacca cttgctcctg gaacttctgg ggcaattaca aaggatccat tgtatctaaa | 360 |
| tcctcagtac ctctaaagga tatcccatcg ggtagtgccc ggaatggata ttgggctttg | 420 |
| agcaatgatg aagttcaaga gattgatcat gtcccttaca acttgagata ttattgttac | 480 |
| tggtgcagaa atgaatatcc tgggagcttt tatatgagat atgtaaagaa agttcggatc | 540 |
| ataagaaatc ctgatgggtc tataaagact cctagaggat cctgggttca tgagttggac | 600 |
| aacttgtggg gagatcagat gaggtatcta gttattcgaa gatttggggg agaatctagc | 660 |
| tgccctctta agatatatga tgtgagagca ggggttctgt caaaatctcg gtcaaacttc | 720 |
| atcttagtgt cccttccctc cttgaatttg cagttctctg tatcacttga atccactgag | 780 |
| acgaaatgct catttggaga taagacatat gatattgtgc agagcatggg aggctatctc | 840 |
| ctctccatcg acataggtaa tgcgaactgg cgaggcccct gggatcctac ccctcagcat | 900 |
| ccgggtcgtg aaagacagtc aattatgcag tttccggatc aaacatcttt cagatataac | 960 |
| caatttataa attatcactc atccccaaga cacaagcagc atgatcaaga atttgagttc | 1020 |
| cctctcagtc taaaatccag ttatgattat gctcaattta gatatgagca gaatttcatc | 1080 |
| atccgacaga tcaataagaa ttttggatta ttacagaaga gcatttgtga tattcagttt | 1140 |
| tctaagtggc agaatctcag tccacccaat cttgctatga aaattgctca ttatgtcacc | 1200 |
| ggctctatcc actctatagg tggtgttcat catggatctt attcaattca aagaacggaa | 1260 |
| aaatccatta ctaaggtcaa tctggtgttt cccattgtta ttgttcatgg aatgtataag | 1320 |
| tgccaaaggg aaccatccaa ggaggtggtt tgggcagaac ccgtcacagg gatcttattc | 1380 |
| aagtctccta ttccgactca tttctcacta gttcctctt ggctacctgg ggtaaatggt | 1440 |
| tcttctattg tccctctgac aggtcaaatt cttctccctg aaatcacaat ggatcacttg | 1500 |
| gaggttgtac aacaggttga agcaaagatg gtcaaaagta tgtacacgaa tgtagagttg | 1560 |
| tttggatcaa cagaggaatt tcaaagatac caaactcagg gaattacctc tgatgaacaa | 1620 |
| tcaaatacag taaatccttg gattgggctt ggtggaagta tgaaacaact tgaagacaag | 1680 |
| gttgaagaat tgctttcgaa aaattatcac ttggaaaatg aggttgccag attaaagaaa | 1740 |
| ttagttggcg aacgctga | 1758 |

<210> SEQ ID NO 19
<211> LENGTH: 1761
<212> TYPE: DNA
<213> ORGANISM: Artificial Sequence
<220> FEATURE:
<223> OTHER INFORMATION: encodes a fusion protein

<400> SEQUENCE: 19

| | | |
|---|---|---|
| atggttttct taagtttatc aacgatcata tttatcctaa gcctccgggc tgtaacctgc | 60 |
| tccaatcctc tctcctatcc taatggcatt ttgactaaca actctactca caatcatccc | 120 |

```
ctatcggact tttatatttt ttatgagaac agttccctta cctatactca attccctgtg    180
gccccagact gctctagtat tctagatact agagatgagc agtatcccac cactgttact    240
ttgtggaagg ttgatcaaga atctcaagct gagtgggggac tccttttatg gcaagagaga   300
attgacacca cttgctcctg gaacttctgg ggcaattaca aaggatccat tgtatctaaa    360
tcctcagtac ctctaaagga tatcccatcg ggtagtgccc ggaatggata ttgggctttg    420
agcaatgatg aagttcaaga gattgatcat gtcccttaca acttgagata ttattgttac    480
tggtgcagaa atgaatatcc tgggagcttt tatatgagat atgtaaagaa agttcggatc    540
ataagaaatc ctgatgggtc tataaagact cctagaggat cctgggttca tgagttggac    600
aacttgtggg gagatcagat gaggtatcta gttattcgaa gatttgggg agaatctagc     660 tgccctctta agatatatga tgtgagagca ggggttctgt caaaatctcg gtcaaacttc    720
atcttagtgt cccttccctc cttgaatttg cagttctctg tatcacttga atccactgag    780
acgaaatgct catttggaga taagacatat gatattgtgc agagcatggg aggctatctc    840
ctctccatcg acataggtaa tgcgaactgg cgaggcccct gggatcctac ccctcagcat    900
ccgggtcgtg aaagacagtc aattatggag tttccggatc aaacatcttt cagatataac    960
caatttataa attatcactc atccccaaga cacaagcagc atgatcaaga atttgagttc    1020
cctctcagtc taaaatccag ttatgattat gctcaattta gatatgagca gaatttcatc    1080
atccgacaga tcaataagaa ttttggatta ttacagaaga gcatttgtga tattcagttt    1140
tctaagtggc agaatctcag tccacccaat cttgctatga aaattgctca ttatgtcacc    1200
ggctctatcc actctatagg tggtgttcat catggatctt attcaattca aagaacggaa    1260
aaatccatta ctaaggtcaa tctggtgttt cccattgtta ttgttcatgg aatgtataag    1320
tgccaaaggg aaccatccaa ggaggtggtt tgggcagaac ccgtcacagg atcttattc    1380 aagtctccta ttccgactca tttctcacta agttcctctt ggctacctgg ggtaaatggt    1440
tcttctattg tccctctgac aggtcaaatt cttctccctg aaatcacaat ggatcacttg    1500
gaggttgtac aacaggttga agcaaagatg gtcaaaagta tgtacacgaa tgtagagttg    1560
tttggatcaa cagaggaatt tcaaagatac caaactcagg gaattacctc tgatgaacaa    1620
tcaaatacag taaatccttg gattgggctt gctagcggag gcggtggagg tggcggaggt    1680
ggttatattc ctgaagctcc aagagatggg caagcttacg ttcgtaaaga tggcgaatgg    1740
gtattgcttt ctacctttt a                                                1761
```

<210> SEQ ID NO 20
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: X at residue 2 can be any amino acid residue
<222> LOCATION: (2)..(2)

<400> SEQUENCE: 20

Arg Xaa Lys Arg
1

<210> SEQ ID NO 21
<211> LENGTH: 4
<212> TYPE: PRT
<213> ORGANISM: Artificial Sequence
<220> FEATURE:
<223> OTHER INFORMATION: furin cleavage site

```
<220> FEATURE:
<221> NAME/KEY: X at residue 2 can be any amino acid residue
<222> LOCATION: (2)..(2)

<400> SEQUENCE: 21

Arg Xaa Arg Arg
1

<210> SEQ ID NO 22
<211> LENGTH: 5
<212> TYPE: PRT
<213> ORGANISM: Artificial Sequence
<220> FEATURE:
<223> OTHER INFORMATION: furin cleavage site
<220> FEATURE:
<221> NAME/KEY: X at residue 2 can be any amino acid residue
<222> LOCATION: (2)..(2)
<220> FEATURE:
<221> NAME/KEY: X at residue 5 can be any amino acid residue other than
      K or other than an amino acid residue selected from the group
      consisting of V, L, I and Y
<222> LOCATION: (5)..(5)

<400> SEQUENCE: 22

Arg Xaa Lys Arg Xaa
1               5

<210> SEQ ID NO 23
<211> LENGTH: 5
<212> TYPE: PRT
<213> ORGANISM: Artificial Sequence
<220> FEATURE:
<223> OTHER INFORMATION: furin cleavage site
<220> FEATURE:
<221> NAME/KEY: X at residue 2 can be any amino acid residue
<222> LOCATION: (2)..(2)
<220> FEATURE:
<221> NAME/KEY: X at residue 5 can be any amino acid residue other than
      K or other than an amino acid residue selected from the group
      consisting of V, L, I and Y
<222> LOCATION: (5)..(5)

<400> SEQUENCE: 23

Arg Xaa Arg Arg Xaa
1               5

<210> SEQ ID NO 24
<211> LENGTH: 6
<212> TYPE: PRT
<213> ORGANISM: Artificial Sequence
<220> FEATURE:
<223> OTHER INFORMATION: furin cleavage site
<220> FEATURE:
<221> NAME/KEY: X at residue 2 can be any amino acid residue
<222> LOCATION: (2)..(2)
<220> FEATURE:
<221> NAME/KEY: X at residue 5 can be any amino acid residue other than
      K or other than an amino acid residue selected from the group
      consisting of V, L, I and Y
<222> LOCATION: (5)..(5)
<220> FEATURE:
<221> NAME/KEY: X at residue 6 can be any amino acid residue other than
      K
<222> LOCATION: (6)..(6)

<400> SEQUENCE: 24

Arg Xaa Lys Arg Xaa Xaa
1               5

<210> SEQ ID NO 25
<211> LENGTH: 6
```

```
<212> TYPE: PRT
<213> ORGANISM: Artificial Sequence
<220> FEATURE:
<223> OTHER INFORMATION: furin cleavage site
<220> FEATURE:
<221> NAME/KEY: X at residue 2 can be any amino acid residue
<222> LOCATION: (2)..(2)
<220> FEATURE:
<221> NAME/KEY: X at residue 5 can be any amino acid residue other than
      K or other than an amino acid residue selected from the group
      consisting of V, L, I and Y
<222> LOCATION: (5)..(5)
<220> FEATURE:
<221> NAME/KEY: X at residue 6 can be any amino acid residue other than
      K
<222> LOCATION: (6)..(6)

<400> SEQUENCE: 25

Arg Xaa Arg Arg Xaa Xaa
1               5
```

POLYPEPTIDES USEFUL FOR DETECTING ANTI-RHABDOVIRUS ANTIBODIES

BACKGROUND OF THE INVENTION

Technical Field

The present invention relates to recombinantly constructed proteins useful for analytical assays, in particular for determining in a biological sample obtained from an individual the presence of antibodies specific for a rhabdovirus.

Background Information

Rhabdoviruses are membrane-enveloped, negative-strand RNA viruses belonging to the family Rhabdoviridae. The rhabodvirus virion comprises an external membrane derived from the cell in which the virus was produced and an internal ribonucleoprotein core comprising the non-segmented genomic RNA and N (nucleocapsid) protein. The rhabdovirus glycoprotein (G) spans the membrane and forms the spikes on the surface of the virus particle. The glycoprotein of rhabdoviruses is known to be essential for virus propagation, due to its functions for both receptor binding and membrane fusion during virus entry. Viral matrix (M) protein molecules are inside the viral envelope and form a layer between the membrane and the nucleocapsid core. The nonstructural proteins include the L (large) and P (phosphoprotein) proteins, which form the viral transcriptase-replicase complex.

Rhabodviruses are widely distributed in nature where they infect vertebrates, invertebrates, and plants. Prototypical rhabdoviruses are rabies virus (RV) and vesicular stomatitis virus (VSV), which are considered to be the most studied of this virus family. In 2014, the discovery of a novel rhabdovirus capable of infecting Spodoptera frugiperda (Sf) cells, and thus termed Sf-rhabdovirus (SfRV), was reported (Ma et al. J Virol. 88(12): 6576-6585). In WO2015051255A1, the detection of this virus by means of a PCR assay was described.

As in practice, for solid phase assays such as ELISA, a certain amount of antigen is needed to be immobilized on a solid support, antigens are desirable which are producible with a highest possible yield in cell culture, in order to reduce the costs per assay and to have less uneconomic waste.

Thus, with regard to the production of a solid phase assay for detecting antibodies specific for a rhabdovirus, a polypeptide is needed which is produced with the highest possible yield in cell culture while retaining the necessary antigenicity for sufficiently binding said antibodies when the assay is performed.

DESCRIPTION OF THE INVENTION

The solution to the above technical problems is achieved by the description and the embodiments characterized in the claims.

Thus, the invention in its different aspects is implemented according to the claims.

The invention is based on the surprising finding that fusing the C-terminus of an ectodomain of a SfRV glycoprotein, preferably having substitutions at amino acid positions 306 and 333, to an IgG Fc domain permitted the expression of a significantly higher molar yield of an antigen usable for detecting antibodies specific for SfRV in a serum sample, when compared with the expression of a respective ectodomain having the wild type sequence. This beneficial effect then also allowed to produce a significantly larger number of ELISA tests with the same costs for protein expression, as compared to the production of comparable tests using the wild type sequence.

In a first aspect, the invention thus relates to a polypeptide comprising
  an ectodomain of a rhabdovirus glycoprotein and
  a heterologous multimerization domain linked to said ectodomain.

Said polypeptide, which is hereinafter also termed "the polypeptide of the present invention", is preferably for determining in a biological sample obtained from an individual the presence of antibodies specific for a rhabdovirus.

As used herein, the term "ectodomain" is intended to encompass that portion of a protein which is located on the outer surface of a virus envelope. For example, the ectodomain of a rhabdovirus glycoprotein is that portion of the rhabdovirus glycoprotein that extends into the extraviral space. More particular, the ectodomain of a rhabdovirus glycoprotein is a rhabdovirus glycoprotein where the transmembrane helix and the cytoplasmic domains have been removed. Still more preferably, the ectodomain of a rhabdovirus glycoprotein is a rhabdovirus glycoprotein where the transmembrane helix, the cytoplasmic domains and the N-terminal signaling peptide have been removed.

The term "multimerization domain" as used in the context of the present invention in particular relates to an amino acid sequence capable to specifically bind to or associate with one or more further multimerization domain(s) such as to form a multimer. In one example, the multimerization domain is an amino acid sequence capable to bind to or, respectively, homoassociate with one other multimerization domain having the same amino acid sequence to form a homodimer. The multimerization domain can contain one or more cysteine residue(s) such that disulfide bond(s) can be formed between the associated multimerization domains.

"Heterologous multimerization domain" in the present context in particular relates to a multimerization domain derived from an entity other than the rhabdovirus from which the rhabdovirus glycoprotein, as mentioned herein, is derived. For example, the heterologous multimerization domain is a multimerization domain encoded by the genome of a virus other than a rhabdovirus or preferably by the genome of an eukaryotic cell or prokaryotic cell, in particular of a mammalian cell.

Preferably, the multimerization domain is linked to said ectodomain via a linker moiety.

The linker moiety, as described herein in the context of the present invention, is preferably a peptide linker.

The term "peptide linker" as used herein refers to a peptide comprising one or more amino acid residues. More particular, the term "peptide linker" as used herein refers to a peptide capable of connecting two variable domains, e.g. an ectodomain and a multimerization domain, with its length depending on the kinds of variable domains to be connected.

In a particular preferred aspect, the multimerization domain is linked to said ectodomain via a linker moiety, wherein
  the multimerization domain is linked to the linker moiety via a peptide bond between the N-terminal amino acid residue of the linker moiety and the C-terminal amino acid residue of the ectodomain and
  the linker moiety is linked to the multimerization domain via a peptide bond between the N-terminal amino acid residue of the multimerization domain and the C-terminal amino acid residue of the linker moiety.

Also, it may be preferred that the multimerization domain is linked to the ectodomain via a peptide bond between the N-terminal amino acid residue of the multimerization domain and the C-terminal amino acid residue of the ectodomain.

In another preferred aspect, the invention provides a polypeptide, in particular the polypeptide as mentioned above, wherein said polypeptide is a fusion protein of the formula x-y-z, wherein
x consists of or comprises an ectodomain of a rhabdovirus glycoprotein;
y is a linker moiety; and
z is a heterologous multimerization domain.

The formula x-y-z is in particular to be understood that the C-terminal amino acid residue of said ectodomain is linked with said linker moiety, preferably via a peptide bond with the N-terminal amino acid residue of said linker moiety, and that the N-terminal amino acid residue of said multimerization domain is linked with said linker moiety, preferably via a peptide bond with the C-terminal amino acid residue of said linker moiety.

Most preferably, the ectodomain mentioned herein in the context of the present invention is free of a furin cleavage site. "Free of a furin cleavage site" particularly means that there is no furin cleavage site present in the amino acid sequence of the ectodomain.

The furin cleavage site, as mentioned herein, is in particular an amino acid sequence selected from the group consisting of the following (a), (b), and (c):
(a) amino acid sequence selected from the group consisting of RXKR (SEQ ID NO:20) and RXRR (SEQ ID NO:21), wherein X can be any amino acid residue;
(b) amino acid sequence selected from the group consisting of $RX_1KRX_2$ (SEQ ID NO:22) and $RX_1RRX_2$ (SEQ ID NO:23), wherein
$X_1$ can be any amino acid residue, and
$X_2$ can be any amino acid residue other than
a lysine residue or
an amino acid residue selected from the group consisting of valine residue, leucine residue, isoleucine residue and tryptophane residue;
(c) amino acid sequence selected from the group consisting of $RX_1KRX_2X_3$ (SEQ ID NO:24) and $RX_1RRX_2X_3$ (SEQ ID NO:25), wherein
$X_1$ can be any amino acid residue,
$X_2$ can be any amino acid residue other than
a lysine residue or
an amino acid residue selected from the group consisting of valine residue, leucine residue, isoleucine residue and tryptophane residue,
and $X_3$ can be any amino residue other than a lysine residue.

The term "any amino acid residue", as described herein, is in particular understood to be equivalent to "any genetically encoded amino acid residue".

The amino acid residue other than a lysine residue, as mentioned herein, is in particular a naturally occurring, preferably a genetically encoded, amino acid residue.

The term "genetically encoded amino acid residue", as described in the context of the present invention, in particular refers to an amino acid residue (single letter code in brackets) selected from the group consisting of alanine residue (A), aspartate residue (D), asparagine residue (N), cysteine residue (C), glutamine residue (Q), glutamate residue (E), phenylalanine residue (F), glycine residue (G), histidine residue (H), isoleucine residue (I), lysine residue (K), leucine residue (L), methionine residue (M), proline residue (P), arginine residue (R), serine residue (S), threonine residue (T), valine residue (V), tryptophan residue (W), and tyrosine residue (Y).

Thus, for instance, the wording "can be any amino acid residue other than a lysine residue", as mentioned herein, is in particular understood to be equivalent to "is an amino acid residue selected from the group consisting of alanine residue, aspartate residue, asparagine residue, cysteine residue, glutamine residue, glutamate residue, phenylalanine residue, glycine residue, histidine residue, isoleucine residue, leucine residue, methionine residue, proline residue, arginine residue, serine residue, threonine residue, valine residue, tryptophan residue, and tyrosine residue".

Most preferably, the rhabdovirus glycoprotein, as mentioned in the context of the present invention, is a *S. frugiperda* rhabdovirus (SF-rhabdovirus) glycoprotein.

In a preferred aspect, the ectodomain as described herein is an ectodomain of a SF-rhabdovirus glycoprotein having
(i) one or more mutations selected from the group consisting of
substitution at amino acid position 306, substitution at amino acid position 303, substitution at amino acid position 305, substitution at amino acid position 307, and substitution at amino acid position 308,
and
(ii) one or more mutations selected from the group consisting of
substitution at amino acid position 333, substitution at amino acid position 330, substitution at amino acid position 332, substitution at amino acid position 334, and substitution at amino acid position 335,
wherein the numbering of the amino acid positions refers to the amino acid sequence of wild type SF-rhabdovirus glycoprotein.

Herein, the term "mutation" covers any change in amino acid sequence (substitutions and insertions with genetically encoded amino acid residues as well as deletions). The term "substitution at amino acid position", as mentioned herein, in particular refers to a change of an amino acid residue at a specific position of the amino acid sequence of a protein.

Preferably, the ectodomain mentioned herein is an ectodomain of a SF-rhabdovirus glycoprotein having one or more of the mutations or amino acid residues described herein, wherein the N-terminal amino acid residue of the ectodomain preferably corresponds to any one of the amino acid positions 1-22, most preferably to the amino acid position 22, 21 or 1, of wild type SF-rhabdovirus glycoprotein.

According to a further preferred aspect the ectodomain described herein comprises or consists of an amino acid sequence being 529-550 amino acid residues in length.

In a particular preferred aspect, said ectodomain is an ectodomain of a SF-rhabdovirus glycoprotein having a substitution at amino acid position 306 and a substitution at amino acid position 333, wherein the numbering of the amino acid positions refers to the amino acid sequence of wild type SF-rhabdovirus glycoprotein.

Preferably, the ectodomain described herein in the context of the present invention is an ectodomain of a SF-rhabdovirus glycoprotein having
at amino acid position 306 an amino acid residue other than an arginine residue, and
at amino acid position 333 an amino acid residue other than an arginine residue, and wherein the numbering of the amino acid positions refers to the amino acid sequence of wild type SF-rhabdovirus glycoprotein.

In a particular preferred aspect, the ectodomain described herein is an ectodomain of a SF-rhabdovirus glycoprotein comprising or consisting of an amino acid sequence having at least 70%, preferably at least 80%, more preferably at least 90% or in particular at least 95% sequence identity with the sequence of SEQ ID NO:4.

The ectodomain mentioned herein is preferably an ectodomain of a SF-rhabdovirus glycoprotein comprising or consisting of an amino acid sequence having at least 70%, preferably at least 80%, more preferably at least 90% or in particular at least 95% sequence identity with the sequence of SEQ ID NO:4 and having
- at amino acid position 306 an amino acid residue other than an arginine residue, and
- at amino acid position 333 an amino acid residue other than an arginine residue, and wherein the numbering of the amino acid positions refers to the amino acid sequence of wild type SF-rhabdovirus glycoprotein.

The term "wherein the numbering of the amino acid positions refers to the amino acid sequence of wild type SF-rhabdovirus glycoprotein" means that the numbering of amino acid positions refers to the amino acid sequence of full length wild type SF-rhabdovirus glycoprotein. Hence, this numbering of the amino positions as mentioned herein is in particular with reference to a wild type SF-rhabdovirus glycoprotein having 610 amino acid residues, including a methionine residue at the (N-terminal) amino acid position 1. Thus, this numbering, as used in the context of the present invention, in particular relates to the sequence of a wild type SF-rhabdovirus glycoprotein, as set forth in SEQ ID NO:16. In other words, in this context, if reference is made to the amino acid position 306, the amino acid residue is meant which corresponds to amino acid 306 of SEQ ID NO:16 or, respectively, if reference is made to the amino acid position 333, the amino acid residue is meant which corresponds to amino acid 333 of SEQ ID NO:16. However, this does not mean that the ectodomain described in such way herein has an amino acid sequence identical to the amino acid sequence of SEQ ID NO:16. It only says that the corresponding amino acid(s) are located at a position within the sequence, which position corresponds to the explicitly mentioned position of the sequence of wild type SF-rhabdovirus glycoprotein. For instance, if it is referred to an ectodomain of a SF-rhabdovirus glycoprotein having an amino acid residue other than an arginine residue at amino acid position 306 and having an amino acid residue other than an arginine residue at amino acid position 333, wherein the numbering of the amino acid positions refers to the amino acid sequence of wild type SF-rhabdovirus glycoprotein, then in one example this would relate to an ectodomain derived from a wild type SF-rhabdovirus glycoprotein of SEQ ID NO:16 containing substitutions at the amino acid positions 306 and 333 (i.e., the arginine residues at the amino acid positions 306 and 333 in the sequence corresponding to SEQ ID NO:16 have each been substituted by an amino acid residue other than an arginine residue).

As an example, the sequence positions 285 and 312 of the ectodomain of SEQ ID NO:1 (i.e. an ectodomain (without N-terminal signaling peptide) of the glycoprotein set forth in SEQ ID NO:16 having a substitution (i.e., a glutamine residue instead of an arginine residue) at each of the amino acid positions 306 and 333) correspond to the amino acid positions 306 and 333 of the amino acid sequence of wild type SF-rhabdovirus glycoprotein, as set forth in SEQ ID NO:16.

It is also understood that the term "signaling peptide" as used herein is equivalent to the term "signaling domain".

According to a further preferred aspect, the ectodomain as described herein is an ectodomain of a SF-rhabdovirus glycoprotein having
- at amino acid position 306 an amino acid residue other than an arginine residue, and/or
- at amino acid position 303 an amino acid residue other than an arginine residue, and/or
- at amino acid position 305 an amino acid residue other than a basic amino acid residue residue, and/or
- at amino acid position 307 an amino acid residue selected from the group consisting of lysine residue, leucine residue, isoleucine residue, valine residue and tryptophane residue, and/or
- at amino acid position 308 a lysine residue, and having
- at amino acid position 333 an amino acid residue other than an arginine residue, and/or
- at amino acid position 330 an amino acid residue other than an arginine residue, and/or
- at amino acid position 332 an amino acid residue other than a basic amino acid residue residue, and/or
- at amino acid position 334 an amino acid residue selected from the group consisting of lysine residue, leucine residue, isoleucine residue, valine residue and tryptophane residue, and/or
- at amino acid position 335 a lysine residue, and wherein the numbering of the amino acid positions refers to the amino acid sequence of wild type SF-rhabdovirus glycoprotein.

The term "basic amino acid residue", as mentioned herein, in particular relates to an amino acid reside selected from the group consisting of arginine residue, lysine residue and histidine residue.

The "amino acid residue other than a basic amino acid residue", as described herein, thus in particular relates to an amino acid residue other than
- an arginine residue,
- a lysine residue or
- a histidine residue.

Preferably, said ectodomain is an ectodomain of a SF-rhabdovirus glycoprotein having
- at amino acid position 306 an amino acid residue other than an arginine residue, and
- at amino acid position 333 an amino acid residue other than an arginine residue, and wherein the numbering of the amino acid positions refers to the amino acid sequence of wild type SF-rhabdovirus glycoprotein.

The wild type SF-rhabdovirus glycoprotein, as mentioned herein, preferably consists of or is the amino acid sequence of SEQ ID NO:16. In this regard, it is in particular understood that the wording "consists of the amino acid sequence" is equivalent to the wording "is the amino acid sequence".

The amino acid sequence of wild type SF-rhabdovirus glycoprotein, as mentioned herein, is thus preferably the amino acid sequence of wild type SF-rhabdovirus glycoprotein of SEQ ID NO:16.

Further, it is in particular preferred according to the present invention if the ectodomain is an ectodomain of a SF-rhabdovirus glycoprotein having at each of the amino acid positions 306 and 333 an amino acid residue other than an arginine residue, wherein the numbering of the amino acid positions refers to the amino acid sequence of wild type SF-rhabdovirus glycoprotein, and wherein said ectodomain consists of an amino acid sequence having at least 70% sequence identity with a sequence selected from the group consisting of SEQ ID NO:1, SEQ ID NO:2 and SEQ ID NO:3.

The amino acid residue other than an arginine residue, as mentioned herein, is in particular a naturally occurring, preferably a genetically encoded, amino acid residue.

According to another preferred aspect, the ectodomain mentioned herein is an ectodomain of a SF-rhabdovirus glycoprotein having
- at amino acid position 306 an amino acid residue selected from the group consisting of amino acid residue with a polar but uncharged side chain, amino acid residue with a hydrophobic side chain, and glycine residue
- and/or at amino acid position 303 an amino acid residue selected from the group consisting of amino acid residue with a polar but uncharged side chain, amino acid residue with a hydrophobic side chain, and glycine residue;
- and
- at amino acid position 333 an amino acid residue selected from the group consisting of amino acid residue with a polar but uncharged side chain, amino acid residue with a hydrophobic side chain, and glycine residue
- and/or at amino acid position 330 an amino acid residue selected from the group consisting of amino acid residue with a polar but uncharged side chain, amino acid residue with a hydrophobic side chain, and glycine residue;
- and wherein the numbering of the amino acid positions refers to the amino acid sequence of wild type SF-rhabdovirus glycoprotein.

The amino acid residue with a polar but uncharged side chain, as mentioned herein in the context of the present invention, is preferably selected from the group consisting of serine residue, threonine residue, tyrosine residue, asparagine residue, and glutamine residue.

The amino acid residue with a hydrophobic side chain, as described herein, is preferably selected from the group consisting of alanine residue, valine residue, leucine residue, methionine residue, isoleucine residue, phenylalanine residue, and tryptophan residue.

According to a more particular preferred aspect, the ectodomain mentioned herein is an ectodomain of a SF-rhabdovirus glycoprotein having
- at amino acid position 306 an amino acid residue selected from the group consisting of glutamine residue and asparagine residue and/or at amino acid position 303 an amino acid residue selected from the group consisting of glutamine residue and asparagine residue; and
- at amino acid position 333 an amino acid residue selected from the group consisting of glutamine residue and asparagine residue and/or at amino acid position 330 an amino acid residue selected from the group consisting of glutamine residue and asparagine residue;
- and wherein the numbering of the amino acid positions refers to the amino acid sequence of wild type SF-rhabdovirus glycoprotein.

Still more particular, an ectodomain is preferred in the context of the present invention, wherein said ectodomain is an ectodomain of a SF-rhabdovirus glycoprotein having
- at amino acid position 306 an amino acid residue selected from the group consisting of glutamine residue and asparagine residue; and
- at amino acid position 333 an amino acid residue selected from the group consisting of glutamine residue and asparagine residue;
- and wherein the numbering of the amino acid positions refers to the amino acid sequence of wild type SF-rhabdovirus glycoprotein.

In another preferred aspect, the ectodomain comprises or consists of an amino acid sequence having at least 70%, preferably at least 80%, more preferably at least 90%, still more preferably at least 95% or in particular 100% sequence identity with a sequence selected from the group consisting of SEQ ID NO:1, SEQ ID NO:2 and SEQ ID NO:3.

In one example, the ectodomain as described herein in the context of the present invention is thus an ectodomain comprising or consisting of an amino acid sequence having at least 70%, preferably at least 80%, more preferably at least 90%, still more preferably at least 95%, sequence identity with the amino acid sequence of SEQ ID NO:1, and wherein the ectodomain has
- at amino acid position 285 an amino acid residue other than an arginine residue, and/or
- at amino acid position 282 an amino acid residue other than an arginine residue, and/or
- at amino acid position 286 an amino acid residue selected from the group consisting of lysine residue, leucine residue, isoleucine residue, valine residue and tryptophane residue, and/or
- at amino acid position 287 a lysine residue,
- and has
- at amino acid position 312 an amino acid residue other than an arginine residue, and/or
- at amino acid position 309 an amino acid residue other than an arginine residue, and/or
- at amino acid position 313 an amino acid residue selected from the group consisting of lysine residue, leucine residue, isoleucine residue, valine residue and tryptophane residue, and/or
- at amino acid position 314 a lysine residue,
- wherein the numbering of the amino acid positions refers to the amino acid sequence of SEQ ID NO:1.

In particular, said ectodomain preferably comprises or consists of an amino acid sequence having at least 70%, preferably at least 80%, more preferably at least 90%, still more preferably at least 95% sequence identity with the amino acid sequence of SEQ ID NO:1, and wherein said ectodomain has
- at amino acid position 285 an amino acid residue other than an arginine residue,
- and
- at amino acid position 312 an amino acid residue other than an arginine residue,
- and wherein the numbering of the amino acid positions refers to the amino acid sequence of SEQ ID NO:1.

More particularly, said ectodomain comprises or consists of an amino acid sequence having at least 70%, preferably at least 80%, more preferably at least 90%, still more preferably at least 95% sequence identity with the amino acid sequence of SEQ ID NO:1, and wherein said ectodomain has
- at amino acid position 285 an amino acid residue selected from the group consisting of amino acid residue with a polar but uncharged side chain, amino acid residue with a hydrophobic side chain, and glycine residue
- and/or at amino acid position 282 an amino acid residue selected from the group consisting of amino acid residue with a polar but uncharged side chain, amino acid residue with a hydrophobic side chain, and glycine residue;
and
at amino acid position 312 an amino acid residue selected from the group consisting of amino acid residue with a polar but uncharged side chain, amino acid residue with a hydrophobic side chain, and glycine residue
and/or at amino acid position 309 an amino acid residue selected from the group consisting of amino acid residue with a polar but uncharged side chain, amino acid residue with a hydrophobic side chain, and glycine residue;
and wherein the numbering of the amino acid positions refers to the amino acid sequence of SEQ ID NO:1.

Still more particularly, said ectodomain comprises or consists of an amino acid sequence having at least 70%, preferably at least 80%, more preferably at least 90%, still more preferably at least 95% sequence identity with the amino acid sequence of SEQ ID NO:1, and wherein said ectodomain has at amino acid position 285 an amino acid residue selected from the group consisting of glutamine residue and asparagine residue and/or at amino acid position 282 an amino acid residue selected from the group consisting of glutamine residue and asparagine residue; and
at amino acid position 312 an amino acid residue selected from the group consisting of glutamine residue and asparagine residue and/or at amino acid position 309 an amino acid residue selected from the group consisting of glutamine residue and asparagine residue;
and wherein the numbering of the amino acid positions refers to the amino acid sequence of SEQ ID NO:1.

The term "wherein the numbering of the amino acid positions refers to the amino acid sequence of SEQ ID NO:1" means that the numbering of amino acid positions refers to the amino acid sequence of the entire sequence of SEQ ID NO:1. Hence, this numbering of amino positions as mentioned herein is with reference to a sequence having 529 amino acid residues, including an asparagine residue at the (N-terminal) amino acid position 1. In other words, in this context, if reference is made to the amino acid position 285, the amino acid residue is meant which corresponds to amino acid 285 of SEQ ID NO:1 or, respectively, if reference is made to the amino acid position 312, the amino acid residue is meant which corresponds to amino acid 312 of SEQ ID NO:1. However, this does not mean that the ectodomain described herein in such a way has an amino acid sequence identical to the amino acid sequence of SEQ ID NO:1. It only says that the corresponding amino acid(s) are located at a position within the sequence, which position corresponds to the explicitly mentioned position of the sequence of SEQ ID NO:1.

Regarding the term "at least 90%", as mentioned in the context of the present invention, it is understood that said term preferably relates to "at least 91%", more preferably to "at least 92%", still more preferably to "at least 93%" or in particular to "at least 94%".

Regarding the term "at least 95%" as mentioned in the context of the present invention, it is understood that said term preferably relates to "at least 96%", more preferably to "at least 97%", still more preferably to "at least 98%" or in particular to "at least 99%".

The term "having 100% sequence identity", as used herein, is understood to be equivalent to the term "being identical".

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2. For purposes of the present invention, nucleotide sequences are aligned using Clustal W method in MegAlign software version 11.1.0 (59), 419 by DNASTAR Inc. using the default multiple alignment parameters set in the program (Gap penalty=15.0, gap length penalty=6.66, delay divergent sequence (%)=30%, DNA transition weight=0.50 and DNA weight matrix=IUB) and, respectively, protein/amino acid sequences are aligned using Clustal W method in MegAlign software software version 11.1.0 (59), 419 by DNASTAR Inc. using the default multiple alignment parameters set in the program (Gonnet series protein weight matrix with Gap penalty=10.0, gap length penalty=0.2, and delay divergent sequence (%)=30%).

As used herein, it is in particular understood that the term "sequence identity with the sequence of SEQ ID NO: X" is equivalent to the term "sequence identity with the sequence of SEQ ID NO: X over the length of SEQ ID NO: X" or to the term "sequence identity with the sequence of SEQ ID NO: X over the whole length of SEQ ID NO: X", respectively. In this context, "X" is any integer selected from 1 to 25 so that "SEQ ID NO: X" represents any of the SEQ ID NOs mentioned herein.

According to a further preferred aspect the ectodomain described herein comprises or consists of an amino acid sequence being 529, 530 or 550 amino acid residues in length.

More particularly, the ectodomain mentioned herein comprises or consists of an amino acid sequence selected from the group consisting of SEQ ID NO:1, SEQ ID NO:2 and SEQ ID NO:3.

The heterologous multimerization domain described herein is preferably selected from the group consisting of immunoglobulin sequence, coiled coil sequence, streptavidin sequence, fibritin sequence, and avidin sequence.

More preferably, the heterologous multimerization domain is selected from the group consisting of immunoglobulin constant region domain, leucine zipper domain and *Escherichia* virus T4 fibritin sequence.

Still more preferably, the heterologous multimerization domain is a dimerization domain, preferably selected from the group consisting of IgG Fc domain and leucine zipper domain.

In particular, it is preferred, if the heterologous multimerization domain comprises or consists of an IgG Fc domain.

If the polypeptide of the present invention is for determining in a biological sample obtained from an individual the presence of antibodies specific for a rhabdovirus, then the amino acid sequence of the immunoglobulin constant region domain, or IgG Fc domain, respectively, as mentioned herein, preferably originates from a biological family other than the biological family of the individual. For example, if the polypeptide of the present invention is for determining in a biological sample obtained from a pig the presence of antibodies specific for a rhabdovirus, then the amino acid sequence of the immunoglobulin constant region domain, or IgG Fc domain, respectively, preferably originates from a biological family other than Suidae. Thus, for instance if said biological sample is obtained from a pig, then the immunoglobulin constant region domain, or IgG Fc domain, respectively is preferably of bovine, canine, goat, sheep, human or guinea pig origin.

More particular, the heterologous multimerization domain preferably comprises or consists of a guinea pig IgG Fc domain.

In a further preferred aspect, the heterologous multimerization domain comprises or consists of an amino acid sequence having at least 70%, preferably at least 80%, more preferably at least 90%, still more preferably at least 95% or in particular 100% sequence identity with a sequence selected from the group consisting of SEQ ID NO:5, SEQ ID NO:6, SEQ ID NO:7 and SEQ ID NO:8.

The linker moiety, or peptide linker, respectively, mentioned herein is preferably an amino acid sequence being 1 to 50 amino acid residues in length, in particular being 3 to 20 amino acid residues in length.

According to a preferred aspect, the linker moiety comprises or consists of an amino acid sequence having at least 66%, preferably at least 80%, more preferably at least 90%, still more preferably at least 95% or in particular 100% sequence identity with a sequence selected from the group consisting of SEQ ID NO:9, SEQ ID NO:10 and SEQ ID NO:11.

In a particular preferred aspect, the polypeptide of the present invention is a protein comprising or consisting of an amino acid sequence having at least 70%, preferably at least 80%, more preferably at least 90%, still more preferably at least 95% sequence identity with a sequence selected from the group consisting of SEQ ID NO:12, SEQ ID NO:13 and SEQ ID NO:14.

Preferably, the polypeptide of the present invention is a protein comprising a sequence selected from the group consisting of SEQ ID NO:12, SEQ ID NO:13 and SEQ ID NO:14.

It is further understood that the term "protein consisting of a sequence", as used herein, in particular also concerns any cotranslational and/or posttranslational modification or modifications of the sequence affected by the cell in which the polypeptide is expressed.

Thus, the term "protein consisting of a sequence", as described herein, is also directed to the sequence having one or more modifications effected by the cell in which the polypeptide is expressed, in particular modifications of amino acid residues effected in the protein biosynthesis and/or protein processing, preferably selected from the group consisting of glycosylations, phosphorylations, and acetylations.

According to a particular preferred aspect of the present invention, in a baculovirus expression system the yield of polypeptide of the present invention polypeptide is higher, preferably by at least a factor 2, more preferably by at least a factor 3, still more preferably by at least a factor 5, yet more preferably by at least a factor 8, compared to the yield of the polypeptide of SEQ ID NO:15.

Thus, the polypeptide of the present invention is preferably a recombinant protein, in particular a recombinant baculovirus expressed protein.

The term "recombinant protein", as used herein, in particular refers to a protein which is produced by recombinant DNA techniques, wherein generally DNA encoding the expressed protein is inserted into a suitable expression vector which is in turn used to transform or, in the case of a virus vector, to infect a host cell to produce the heterologous protein. Thus, the term "recombinant protein", as used herein, particularly refers to a protein molecule that is expressed from a recombinant DNA molecule. "Recombinant DNA molecule" as used herein refers to a DNA molecule that is comprised of segments of DNA joined together by means of molecular biological techniques. Suitable systems for production of recombinant proteins include but are not limited to insect cells (e.g., baculovirus), prokaryotic systems (e.g., *Escherichia coli*), yeast (e.g., *Saccharomyces cerevisiae, Pichia pastoris*), mammalian cells (e.g., Chinese hamster ovary, HEK293), plants (e.g., safflower), avian cells, amphibian cells, fish cells, and cell-free systems (e.g., rabbit reticulocyte lysate).

The term "yield", as mentioned herein, is in particular understood to be "molar yield".

According to another aspect, the invention also provides a polynucleotide which encodes the polypeptide of the present invention, wherein said polynucleotide is also termed "the polynucleotide according to the present invention" hereinafter.

Preferably, the polynucleotide according to the present invention comprises a nucleotide sequence having at least 70%, preferably at least 80%, more preferably at least 90%, still more preferably at least 95% or in particular 100% sequence identity with a sequence selected from the group consisting of SEQ ID NO:17, SEQ ID NO:18 and SEQ ID NO:19.

Production of the polynucleotides described herein is within the skill in the art and can be carried out according to recombinant techniques described, among other places, in Sam brook et al., 2001, Molecular Cloning, A Laboratory Manual, Cold Spring Harbor Laboratory Press, Cold Spring Harbor, N.Y.; Amusable, et al., 2003, Current Protocols In Molecular Biology, Greene Publishing Associates & Wiley Interscience, NY; Innis et al. (eds), 1995, PCR Strategies, Academic Press, Inc., San Diego; and Erlich (ed), 1994, PCR Technology, Oxford University Press, New York, all of which are incorporated herein by reference.

In still a further aspect, the present invention provides a vector containing a polynucleotide which encodes the polypeptide of the present invention.

"Vector" as well as "vector containing a polynucleotide which encodes the polypeptide of the present invention", for purposes of the present invention, refers to a suitable expression vector, preferably a baculovirus expression vector, which is in turn used to transfect, or in case of a baculovirus expression vector to infect, a host cell to produce the protein or polypeptide encoded by the DNA. Vectors and methods for making and/or using vectors (or recombinants) for expression can be made or done by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382,425, PCT publications WO 94/16716, WO 96/39491, WO 95/30018; Paoletti, "Applications of pox virus vectors to vaccination: An update, "PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector, "Molecular and Cellular Biology March 1984, Vol. 4, No. 3, p. 406; EPA0 370 573; U.S. application No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Feigner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589, 466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

Preferred viral vectors include baculovirus such as BaculoGold (BD Biosciences Pharmingen, San Diego, Calif.), in particular provided that the production cells are insect cells. Although the baculovirus expression system is preferred, it is understood by those of skill in the art that other expression systems, including those described above, will work for purposes of the present invention, namely the expression of recombinant protein.

Thus, the invention also provides a baculovirus containing a polynucleotide which encodes the polypeptide of the present invention, wherein said baculovirus is also termed "the baculovirus according to the present invention" hereinafter.

Furthermore, a plasmid is provided by the present invention, wherein said plasmid comprises a polynucleotide which encodes the polypeptide of the present invention. Said plasmid is also termed "the plasmid according to the present invention" hereinafter, and is preferably an expression vector.

The invention further provides a cell, which comprises a plasmid, in particular an expression vector, which comprises a polynucleotide encoding the polypeptide of the present invention, or which is infected with a baculovirus which contains a polynucleotide encoding the polypeptide of the present invention, and wherein said cell is also termed "the cell according to the present invention" hereinafter.

In another specific aspect, the plasmid according to the present invention, the cell according to the present invention, or the baculovirus according to present invention, respectively, contains a polynucleotide comprising a nucleotide sequence having at least 70%, preferably at least 80%, more preferably at least 90%, still more preferably at least 95% or in particular 100% sequence identity with a sequence selected from the group consisting of SEQ ID NO:17, SEQ ID NO:18 and SEQ ID NO:19.

In still another aspect, the present invention provides a kit containing the polypeptide of the present invention immobilized to a solid support.

As used herein the term "immobilized" particularly means that the polypeptide of the present invention can be attached to a surface (e.g., the solid support) in any manner or any method; including, e.g., reversible or non-reversible binding, covalent or non-covalent attachment, and the like.

The term "solid support", as mentioned herein, denotes a non-fluid substance, and includes chips, vessels, and particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid support component of an assay is distinguished from inert solid surfaces with which the assay may be in contact in that a "solid support" contains at least one moiety on its surface, which is intended to interact with the capture reagent, either directly or indirectly. A solid support may be a stationary component, such as a tube, strip, cuvette, or microtiter plate, or may be non-stationary components, such as beads and microparticles. Microparticles can also be used as a solid support for homogeneous assay formats. A variety of microparticles that allow both non-covalent or covalent attachment of proteins and other substances may be used. Such particles include polymer particles such as polystyrene and poly(methylmethacrylate); gold particles such as gold nanoparticles and gold colloids; and ceramic particles such as silica, glass, and metal oxide particles. See for example Martin, C. R., et al., Analytical Chemistry-News & Features 70 (1998) 322A-327A, which is incorporated herein by reference.

A "chip" is a solid, non-porous material, such as metal, glass or plastics. The material may optionally be coated, entirely or in certain areas. On the surface of the material any array of spots is present, either visible or in coordinates. On each spot a defined polypeptide, with or without linker or spacer to the surface of the material, may be immobilized. All documents mentioned herein, both supra and infra, are hereby incorporated herein by reference.

In still another aspect of the present invention, a method of producing the polypeptide of the present invention is provided, wherein the method comprises transfecting a cell with a plasmid, preferably an expression vector, which comprises a polynucleotide comprising a sequence which encodes the polypeptide of the present invention, or infecting a cell, preferably an insect cell, with a baculovirus containing a polynucleotide comprising a sequence which encodes the polypeptide of the present invention.

In a specific aspect of the method of producing the polypeptide of the present invention, said plasmid is the plasmid according to the present invention, in particular as mentioned above.

In another specific aspect of the method of producing the polypeptide of the present invention, said baculovirus is the baculovirus according to the present invention, in particular as mentioned above.

The invention further provides a method of determining in a biological sample obtained from an individual the presence or absence of antibodies specific for a rhabdovirus, wherein said method comprises the steps of:

a. contacting the biological sample with a capture reagent immobilized to a solid support, wherein the capture reagent is the polypeptide of the present invention; and
b. determining the presence or absence of said antibodies bound to said capture reagent.

Preferably, said method of determining in a biological sample obtained from an individual the presence or absence of antibodies specific for a rhabdovirus further comprises the steps of:

c. separating the biological sample from the immobilized capture reagent;
d. contacting the immobilized capture reagent-antibody complex with a detectable agent that binds to the antibody of the reagent-antibody complex; and
e. measuring the level of antibody bound to the capture reagent using a detection means for the detectable agent, and wherein the measuring step (e.) preferably further comprises a comparison with a standard curve to determine the level of antibody bound to the capture reagent.

Said detectable agent that binds to the antibody of the reagent-antibody complex is preferably a detectable antibody, more preferably a labelled secondary antibody.

The term "biological sample" as used herein refers to any sample that is taken from an individual (e.g. from a pig or a bird) and includes, without limitation, cell-containing bodily fluids, peripheral blood, blood plasma or serum, saliva, tissue homogenates, lung and other organ aspirates, and lavage and enema solutions, and any other source that is obtainable from a human or animal subject. For animals, examples of a "biological sample" include blood, cells, feces, diarrhea, milk, mucus, phlegm, pus, saliva, semen, sweat, tear, urine, tears, ocular fluids, vaginal secretions, and vomit, if present in that animal.

The biological sample, as referred to herein, has preferably been isolated from a mammal or a bird, preferably from a pig or a chicken (*Gallus gallus domesticus*), and/or is in particular selected from the group consisting of whole blood, blood plasma, serum, urine, and oral fluids. Herein, the term "serum" is meant to be equivalent to "blood serum".

The term "oral fluids" as used herein, in particular refers to one or more fluids found in the oral cavity individually or in combination. These include, but are not limited to saliva and mucosal transudate. It is particularly understood that oral fluids can comprise a combination of fluids from a number of sources (e.g., parotid, submandibular, sublingual, accessory glands, gingival mucosa and buccal mucosa) and the term "oral fluids" includes the fluids from each of these sources individually, or in combination. The term "saliva" refers to a combination of oral fluids such as is typically found in the mouth, in particular after chewing. The term "mucosal transudate", as used herein, refers to fluid produced by the passive diffusion of serum components from oral mucosal interstitia into the oral cavity. Mucosal transudate often forms one component of saliva.

Preferably, the antibodies as described herein are polyclonal antibodies.

The term "antibodies specific for a rhabdovirus" is in particular equivalent to "antibodies specific for an antigen of a rhabdovirus", and wherein said antigen is preferably a rhabdovirus glycoprotein.

A rhabdovirus glycoprotein in the context of the present invention is most preferably the SF-rhabdovirus glycoprotein set forth in SEQ ID NO:16.

The term "antigen", as used herein, in particular refers to any molecule, moiety or entity capable of eliciting an immune response. This includes cellular and/or humoral immune responses.

As used herein, the term "antibodies specific for" a defined antigen in particular refers to antibodies, preferably polyclonal antibodies, that bind an antigen with an affinity or $K_a$ (i.e., an equilibrium association constant of a particular binding interaction with units of 1/M) of, for example, greater than or equal to about $10^5$ $M^{-1}$, $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$ or $10^{13}$ $M^{-1}$. Alternatively, binding affinity may be defined as an equilibrium dissociation constant ($K_d$) of a particular binding interaction with units of M (e.g., $10^{-5}$ M to $10^{-13}$ M). Binding affinities of antibodies can be readily determined using techniques well known to those of skill in the art (see, e.g., Scatchard et al. (1949) Ann. N.Y. Acad. Sci. 51:660; U.S. Pat. Nos. 5,283,173; 5,468,614; BIACORE® analysis; or the equivalent).

The immobilized capture reagent, as described herein, is preferably coated on a microtiter plate, in particular to a microtiter plate capable to be read out by an ELISA reader.

"Insect cell" as used herein means a cell or cell culture derived from an insect species. Of particular interest with respect to the present invention are insect cells derived from the species *Spodoptera frugiperda* and *Trichoplusia ni*.

The *Spodoptera Frugiperda* (Sf) cell is preferably selected from the group consisting of Sf9 cell and Sf+ cell. Respectively, the insect cells, as mentioned herein, are preferably *Spodoptera Frugiperda* (Sf) cells, and are preferably selected from the group consisting of Sf9 cells and Sf+ cells.

The invention further concerns the use of the polypeptide of the present invention in a method for determining in a biological sample obtained from an individual the presence or absence of antibodies specific for a rhabdovirus, wherein said method is preferably the respective method as described above.

Also, the invention relates to the use of the polypeptide of the present invention in a method for determining whether an individual has received an immunogenic composition comprising a recombinant protein produced by an expression system in cultured insect cells, wherein said method is preferably a respective method as described above.

EXAMPLES

The following examples are only intended to illustrate to the present invention. They shall not limit the scope of the claims in any way.

Example 1

Sf rhabdovirus glycoprotein (SFRVG) Baculoviral Expression Constructs

An SFRVG ectodomain was initially generated, by removing the transmembrane helix and cytoplasmic domains of SFRVG. A further modification was to fuse wild type and mutant SFRV ecto to an immunoglobulin G fragment crystallizable (IgG Fc) protein.

SfRV glycoprotein ectodomain (SFRVGecto) has been cloned, inserted into a baculoviral transfer plasmid, and recombinant baculovirus generated to express SFRVGecto. Successive iterations of recombinant baculoviruses were made resulting in a recombinant baculovirus that could express full length SFRVGecto which could subsequently be recovered in high molar quantity.

Discovery of Furin Cleavage Sites in SFRVG

Secondary structure prediction programs Jpred (http://www.compbio.dundee.ac.uk/jpred/) and PSIPRED (http://bioinf.cs.ucl.ac.uk/psipred/) were used to locate coiled regions in SFRVG (SEQ ID NO:16) while Globplot (http://globplot.embl.de/) was used to find predicted regions of disorder as such regions are anticipated to be more sensitive to proteolytic cleavage. These programs predicted a large coiled region roughly comprising amino acids 285-335 (numbering according to the immature protein) that overlapped with a disordered region roughly comprising amino acids 285-305. Review of this region identified a highly charged region with sequence RERR from amino acid 303 to 306, which is a furin protease site with presumed cleavage site following the final arginine. The proprotein convertase recognition site prediction program ProP (http://www.cbs.dtu.dk/services/ProP/; Duckert, 2004) was then used to confirm the furin site. Not only was this position predicted with high confidence to be a furin site, a second site within the largely coiled region from amino acid 330 to 333 with sequence RHKR was also predicted to be cleavable by furin.

Removal of SFRVG Furin Sites

Site-directed mutagenesis was performed to remove the furin sites from SFRVG. Three different mutations to SFRVGecto were then made: R306Q, R333Q, and R306Q/R333Q, which were then assessed for their ability to express SFRVGecto. The SFRVGecto sequence used for this purpose contained the first 550 amino acids of SFRVG, including the native signaling peptide, fused (C-term) to a TEV protease site followed by a 6×His tag.

Point mutants were generated as follows: the first 550 amino acids that comprise the SFRVG ectodomain were PCR amplified, gel purified, and TOPO cloned. Following verification of the insert by colony screen by PCR and DNA sequencing, R306Q and R333Q point mutations were individually made using a QuikChange Lightning Site Directed Mutagenesis kit (Agilent, cat #000628596). Inserts were verified by DNA sequencing, and using TOPO-SFRVGecto-R306Q as the template the R306Q/R333Q double mutant was made and subsequently verified by DNA sequencing. All three TOPO-SFRVGecto mutants were EcoRI/PstI digested, and gel purified while pVL1393 was EcoRI/PstI digested, dephosphorylated, and gel purified. Ligations were done using T4 DNA ligase. Inserts into pVL1393 were verified by colony screen by PCR and DNA sequencing. Baculoviruses were generated by co-transfecting with FlashBAC ULTRA (FBU) into Sf9 cells. IFAs were performed using anti-baculovirus envelope gp64 purified clone AcV1 (eBiosciences, cat #14-6991-83) or anti-His (C-term; Invitrogen, cat #46-0693) primary antibodies at 1:100 and FITC-conjugated goat anti-mouse (JIR, cat #115-095-003) secondary antibody, also at 1:100 dilution. Sf9 cells transfected with pVL1393-SFRVGecto-R306Q, -R333Q, or -R306Q/R333Q plasmids were positive for both 6×His and baculovirus gp64 protein.

FBU/pVL1393-SFRVGecto-R306Q, -R333Q, and -R306Q/R333Q baculoviruses were expanded on T25 flasks of Sf9 cells for six days and P2 baculoviruses titered. P3 expansion and protein expression trials were done by inoculating 100 mL of Sf+ cells in 500 mL spinner flasks at 0.1 MOI. Samples of spent media and cells were harvested 3-5 DPI (Days Post Infection) with the remaining culture harvested 5 DPI. Cell pellets were lysed in buffer containing 1% Triton X-100, and samples centrifuged 20 minutes at 20,000 g. Resulting samples were run out on SDS-PAGE, transferred to nitrocellulose, and western blot probed with 1:500 dilution of anti-His (C-term; Invitrogen, cat #46-0693) primary antibody and 1:1000 dilution of HRP-conjugated goat anti-mouse (JIR, cat #115-035-146) secondary antibody Fusion of SFRVG Ectodomain to Swine Immunoglobulin G 2a Fragment Crystallizable (IgG Fc)

To aid in expression of SFRVG and provide a means of protein purification SFRVGecto-R306Q/R333Q was fused to a swine IgG 2a Fc domain (said IgG Fc domain having the sequence of SEQ ID NO:6). Simultaneously SFRVGecto with the furin sites intact (SFRVGecto-WT) was also fused to an IgG Fc to determine if in the context of a fusion protein removal of the two furin sites was required. Assembly of the two protein coding sequences and insertion into pVL1393 baculovirus transfer plasmid is briefly as follows: primers for amplifying SFRVGecto and IgG Fc were received and SFRVGecto-WT, SFRVG-R306Q/R333Q, and IgG Fc were amplified by PCR, gel purified, and OEPCR done to generate the fusion protein inserts. OEPCR products were gel purified and TOPO cloned, with inserts verified by colony screen by PCR and DNA sequencing. TOPO clones containing the SFRVGecto-WT-IgG2a and SFRVGecto-R306Q/R333Q-IgG2a inserts were EcoRI/PstI digested and gel purified while pVL1393 was EcoRI/PstI digested, dephosphorylated, and gel purified. Ligations were done using T4 DNA ligase with inserts verified by colony screen by PCR and DNA sequencing.

Baculoviruses were generated by co-transfecting pVL1393-SFRVGecto-R306Q/R333Q-IgG2a or pVL1393-SFRVGecto-WT-IgG2a with FlashBAC ULTRA (FBU) into Sf9 cells. IFAs were performed using anti-baculovirus envelope gp64 purified clone AcV1 (eBiosciences, cat #14-6991-83) primary antibody at 1:100 and FITC-conjugated goat anti-mouse (JIR, cat #115-095-003) secondary antibody, also at 1:00 dilution. Sf9 cells transfected with either pVL1393 plasmid were positive for baculovirus gp64 protein. Both FBU/pVL1393-SFRVGecto-R306Q/R333Q-IgG2a and FBU/pVL1393-SFRVGecto-WT-IgG2a baculoviruses were expanded on T25 flasks of Sf9 cells for six days and P2 baculoviruses titered.

P3 expansion and protein expression trials were done by inoculating 100 mL of Sf+ cells in 500 mL spinner flasks with either baculovirus at 0.1 MOI. Samples of spent media and cells were harvested 3 and 4 DPI with the remaining culture harvested 4 DPI. Cell pellets were lysed in buffer containing 1% Triton X-100, and samples centrifuged 20 minutes at 20,000 g.

Resulting samples were run out on SDS-PAGE, transferred to nitrocellulose, and western blot probed with 1:1000 dilution of HRP-conjugated goat anti-swine (JIR, cat #115-035-003) antibody.

From the experiments including the above described SDS Page and Western Blot analyses it was seen that (i) the fusion of the SFRVG ectodomain to Swine Immunoglobulin G 2a Fragment Crystallizable (IgG Fc), or (ii) the SFRVG ectodomain having one of the substitutions (R306Q or R333Q), respectively, resulted in a significantly higher molar yield in the expression system as compared to the expression of the respective unmodified SFRVG ectodomain.

Further, it was found that the combination of both substitutions R306Q and R333Q within the SFRVG ectodomain resulted in a significantly higher molar yield as compared to the expression of SFRVG ectodomain having only one of these substitutions (R306Q or R333Q).

Finally, it was then surprisingly seen that the combination of the above modifications resulted in a synergistic effect, as it was found that the expression of the SFRV ectodomain with both substitutions R306Q/R333Q fused to IgG2a (pVL1393-SFRVGecto-R306Q/R333Q-IgG2a), revealed a much higher yield (by at least a factor 8) as compared to the expression of
- the respective SFRVG wild type ectodomain fused to IgG2a (pVL1393-SFRVGecto-WT-IgG2a) or
- the SFRVG ectodomains having both substitutions R306Q and R333Q (pVL1393-SFRVGecto-R306Q/R333Q).

A respective synergistic effect, resulting in a much higher yield, was also observed for a corresponding combination including a guinea pig IgG Fc domain, namely for a fusion protein comprising the sequence of SEQ ID NO:1. Furthermore, said sequence of SEQ ID NO:1 can be linked via a linker to the guinea pig IgG Fc domain, e.g. to the sequence of SEQ ID NO:5. Therefore, in particular, a respective synergistic effect, resulting in a much higher yield, was observed for a fusion protein having the sequence of SEQ ID NO:12, which comprises the sequence of SEQ ID NO:1 and the sequence of SEQ ID NO:5 linked to said sequence of SEQ ID NO:1 via a peptide linker.

Example 2

An ELISA is employed to evaluate the presence of anti-rhabdovirus antibodies in different liquid samples.

For this purpose, a fusion protein of the above-mentioned formula x-y-z is immobilized as the antigen to an ELISA plate (with x being the ectodomain of a glycoprotein of the rhabdovirus for which the antibodies to be detected are specific, y being a peptide linker and z being an IgG Fc domain), wherein for example the fusion protein comprising the sequence of SEQ ID NO:12 is immobilized.

The ELISA method used in this context is described in the following protocol:
1. Coat plates or strips with 5-500 ng/well of antigen (include plates with different binding capacities, material (polystyrene etc), formats (strips/96 well plates) etc). Incubate overnight at 2-8° C. for binding.
2. Wash plates and block wells with blocking buffer containing 2-10% non fat milk in PBS and 0.5-10% additional protein including BSA/non-relevant serum.
3. After the blocking step, wash plates in a plate washer and tap plate on a wad of paper towels to get rid of remaining wash fluids.
4. Dilute test serum 1:100 and add 100 µL diluted test serum per well. Add 100 µL negative control serum (and, where necessary, positive control serum), diluted 1:100, to control wells.
5. Tap side of plates to shake and mix. Seal the plate/strip and incubate at 37° C. (98.6° F.) for 1 hour.
6. Wash plates in a plate washer and tap plate on a wad of paper towels to get rid of remaining wash fluids.
7. Add 100 µL of pre-diluted (dilution 1:1000-1:100000) HRP Conjugate (e.g. anti-pig IgG (whole molecule), HRP conjugated) to each well. Seal the plate and incubate at 37° C. for 1 hour.
8. Wash plates in a plate washer and tap plate on a wad of paper towels to get rid of remaining wash fluids.
9. Add 100 µL of Substrate Solution to each well. Incubate for 10 minutes at room temperature. Start timer when the first well is filled.
10. Stop the reaction by adding 50 µL of Stop Solution to each well and mix gently by tapping sides.
11. Measure the OD at 450 nm within 15 minutes after the addition of Stop Solution to prevent fluctuation in OD values.

The results of the ELISA show a clear difference between the samples containing the anti-rhabdovirus antibodies to be detected (said samples showing e.g. a S/P ratio of above 0.5) and the negative controls (i.e. corresponding samples not containing such antibodies, which show e.g. a S/P ratio of approx. 0).

In conclusion, the use of the polypeptide of the present invention for detecting anti-rhabdovirus antibodies allows to readily discern samples including anti-rhabdovirus antibodies from samples not including such antibodies.

In the Sequence Listing:

SEQ ID NO:1 corresponds to the sequence of an ectodomain (without N-terminal signaling peptide) of the glycoprotein set forth in SEQ ID NO:16 having a substitution (i.e., a glutamine residue instead of an arginine residue) at each of the amino acid positions 306 and 333, and wherein said amino acid positions of SEQ ID NO:16 correspond to the sequence positions 285 and 312 of SEQ ID NO:1, SEQ ID NO:2 corresponds to the sequence of SEQ ID NO:1 N-terminally extended by a serine residue (corresponding to the serine residue at amino acid position 21 of SEQ ID NO:16), SEQ ID NO:3 corresponds to the sequence of SEQ ID NO:1 N-terminally extended by the N-terminal 21 amino acid residues (i.e., including the N-terminal signaling peptide) of SEQ ID NO:16, SEQ ID NO:4 corresponds to the sequence of the glycoprotein set forth in SEQ ID NO:16 having a substitution (i.e., a glutamine residue instead of an arginine residue) at each of the amino acid positions 306 and 333, SEQ ID NO:5 corresponds to the sequence of a guinea pig IgG Fc domain, SEQ ID NO:6 corresponds to the sequence of a swine IgG Fc domain, SEQ ID NO:7 corresponds to the sequence of a GCN4 leucine zipper domain, SEQ ID NO:8 corresponds to an *Escherichia* virus T4 fibritin sequence, SEQ ID NO:9 corresponds to the sequence of a linker moiety, SEQ ID NO:10 corresponds to the sequence of a linker moiety, SEQ ID NO:11 corresponds to the sequence of a linker moiety, SEQ ID NO:12 corresponds to the sequence of a polypeptide of the present invention, SEQ ID NO:13 corresponds to the sequence of a polypeptide of the present invention, SEQ ID NO:14 corresponds to the sequence of a polypeptide of the present invention, SEQ ID NO:15 corresponds to the sequence of an ectodomain of the wild type glycoprotein set forth in SEQ ID NO:16, SEQ ID NO:16 corresponds to the sequence of a wild type Sf-rhabdovirus glycoprotein, SEQ ID NO:17 corresponds to the sequence of a polynucleotide encoding a polypeptide of the present invention, SEQ ID NO:18 corresponds to the sequence of a polynucleotide encoding a polypeptide of the present invention, SEQ ID NO:19 corresponds to the sequence of a polynucleotide encoding a polypeptide of the present invention, SEQ ID NO:20 corresponds to the sequence of a furin cleavage site, SEQ ID NO:21 corresponds to the sequence of a furin cleavage site, SEQ ID NO:22 corresponds to the sequence of a furin cleavage site, SEQ ID NO:23 corresponds to the sequence of a furin cleavage site, SEQ ID NO:24 corresponds to the sequence of a furin cleavage site, SEQ ID NO:25 corresponds to the sequence of a furin cleavage site.

The following clauses are also disclosed herein:

1. A polypeptide comprising
   an ectodomain of a rhabdovirus glycoprotein, and
   a heterologous multimerization domain linked to said ectodomain.
2. The polypeptide of clause 1,
   wherein said heterologous multimerization domain is linked to said ectodomain via a linker moiety,
   or wherein said heterologous multimerization domain is linked to said ectodomain via a peptide bond between the N-terminal amino acid residue of said heterologous multimerization domain and the C-terminal amino acid residue of said ectodomain.
3. A polypeptide, in particular the polypeptide of clause 1 or 2, wherein said polypeptide is a fusion protein of the formula x-y-z, wherein
   x consists of or comprises an ectodomain of a rhabdovirus glycoprotein;
   y is a linker moiety; and
   z is a heterologous multimerization domain.
4. The polypeptide of any one of clauses 1 to 3, wherein said ectodomain is free of a furin cleavage site.
5. The polypeptide of clause 4, wherein said furin cleavage site is an amino acid sequence selected from the group consisting of the following (a), (b), and (c):
   (a) amino acid sequence selected from the group consisting of RXKR (SEQ ID NO:20) and RXRR (SEQ ID NO:21);
   (b) amino acid sequence selected from the group consisting of $RX_1KRX_2$ (SEQ ID NO:22) and $RX_1RRX_2$ (SEQ ID NO:23), wherein
   $X_1$ can be any amino acid residue, and
   $X_2$ can be any amino acid residue other than
      a lysine residue or
      an amino acid residue selected from the group consisting of valine residue, leucine residue, isoleucine residue and tryptophane residue;
   (c) amino acid sequence selected from the group consisting of $RX_1KRX_2X_3$ (SEQ ID NO:24) and $RX_1RRX_2X_3$ (SEQ ID NO:25), wherein
   $X_1$ can be any amino acid residue,
   $X_2$ can be any amino acid residue other than
      a lysine residue or
      an amino acid residue selected from the group consisting of valine residue, leucine residue, isoleucine residue and tryptophane residue,
   and $X_3$ can be any amino residue other than a lysine residue.
6. The polypeptide of any one of clauses 1 to 5, wherein said rhabdovirus glycoprotein is a *S. frugiperda* rhabdovirus (SF-rhabdovirus) glycoprotein.
7. The polypeptide of any one of clauses 1 to 6, wherein said ectodomain is an ectodomain of a SF-rhabdovirus glycoprotein having
   (i) one or more mutations selected from the group consisting of substitution at amino acid position 306, substitution at amino acid position 303, substitution at amino acid position 305, substitution at amino acid position 307, and substitution at amino acid position 308,
   and
   (ii) one or more mutations selected from the group consisting of substitution at amino acid position 333, substitution at amino acid position 330, substitution at amino acid position 332, substitution at amino acid position 334, and substitution at amino acid position 335,
   wherein the numbering of the amino acid positions refers to the amino acid sequence of wild type SF-rhabdovirus glycoprotein.
8. The polypeptide of any one of clauses 1 to 7, wherein said ectodomain is an ectodomain of a SF-rhabdovirus glycoprotein comprising or consisting of an amino acid sequence having at least 70%, preferably at least 80%, more preferably at least 90% or in particular at least 95% sequence identity with the sequence of SEQ ID NO:4.
9. The polypeptide of any one of clauses 1 to 8, wherein said ectodomain is an ectodomain of a SF-rhabdovirus glycoprotein having
   at amino acid position 306 an amino acid residue other than an arginine residue, and/or
   at amino acid position 303 an amino acid residue other than an arginine residue, and/or
   at amino acid position 305 an amino acid residue other than a basic amino acid residue, and/or
   at amino acid position 307 an amino acid residue selected from the group consisting of lysine residue, leucine residue, isoleucine residue, valine residue and tryptophane residue, and/or
   at amino acid position 308 a lysine residue,
   and having
   at amino acid position 333 an amino acid residue other than an arginine residue, and/or at amino acid position 330 an amino acid residue other than an arginine residue, and/or at amino acid position 332 an amino acid residue other than a basic amino acid residue, and/or at amino acid position 334 an amino acid residue selected from the group consisting of lysine residue, leucine residue, isoleucine residue, valine residue and tryptophane residue, and/or at amino acid position 335 a lysine residue, and wherein the numbering of the amino acid positions refers to the amino acid sequence of wild type SF-rhabdovirus glycoprotein.

10. The polypeptide of any one of clauses 1 to 9, wherein said ectodomain is an ectodomain of a SF-rhabdovirus glycoprotein having at amino acid position 306 an amino acid residue other than an arginine residue, and at amino acid position 333 an amino acid residue other than an arginine residue, and wherein the numbering of the amino acid positions refers to the amino acid sequence of wild type SF-rhabdovirus glycoprotein.

11. The polypeptide of any one of clauses 1 to 10, wherein said ectodomain is an ectodomain of a SF-rhabdovirus glycoprotein comprising or consisting of an amino acid sequence having at least 70%, preferably at least 80%, more preferably at least 90% or in particular at least 95% sequence identity with the sequence of SEQ ID NO:4 and having at amino acid position 306 an amino acid residue other than an arginine residue, and at amino acid position 333 an amino acid residue other than an arginine residue, and wherein the numbering of the amino acid positions refers to the amino acid sequence of wild type SF-rhabdovirus glycoprotein.

12. The polypeptide of any one of clauses 9 to 11, wherein said amino acid residue other than an arginine residue is a naturally occurring, preferably a genetically encoded, amino acid residue.

13. The polypeptide of any one of clauses 6 to 12, wherein the N-terminal amino acid residue of said ectodomain corresponds to any one of the amino acid positions 1-22 of the amino acid sequence of wild type SF-rhabdovirus glycoprotein.

14. The polypeptide of any one of clauses 6 to 13, wherein the N-terminal amino acid residue of said ectodomain corresponds to any one of the amino acid positions 22, 21 or 1 of the amino acid sequence of wild type SF-rhabdovirus glycoprotein.

15. The polypeptide of any one of clauses 1 to 14, wherein said ectodomain is an ectodomain of a SF-rhabdovirus glycoprotein having at amino acid position 306 an amino acid residue selected from the group consisting of amino acid residue with a polar but uncharged side chain, amino acid residue with a hydrophobic side chain, and glycine residue and/or at amino acid position 303 an amino acid residue selected from the group consisting of amino acid residue with a polar but uncharged side chain, amino acid residue with a hydrophobic side chain, and glycine residue;

and at amino acid position 333 an amino acid residue selected from the group consisting of amino acid residue with a polar but uncharged side chain, amino acid residue with a hydrophobic side chain, and glycine residue and/or at amino acid position 330 an amino acid residue selected from the group consisting of amino acid residue with a polar but uncharged side chain, amino acid residue with a hydrophobic side chain, and glycine residue;

and wherein the numbering of the amino acid positions refers to the amino acid sequence of wild type SF-rhabdovirus glycoprotein.

16. The polypeptide of clause 15, wherein said amino acid residue with a polar but uncharged side chain is selected from the group consisting of serine residue, threonine residue, tyrosine residue, asparagine residue, and glutamine residue, and/or wherein said amino acid residue with a hydrophobic side chain is selected from the group consisting of alanine residue, valine residue, leucine residue, methionine residue, isoleucine residue, phenylalanine residue, and tryptophan residue.

17. The polypeptide of any one of clauses 1 to 16, wherein said ectodomain is an ectodomain of a SF-rhabdovirus glycoprotein having at amino acid position 306 an amino acid residue selected from the group consisting of glutamine residue and asparagine residue and/or at amino acid position 303 an amino acid residue selected from the group consisting of glutamine residue and asparagine residue;

and at amino acid position 333 an amino acid residue selected from the group consisting of glutamine residue and asparagine residue and/or at amino acid position 330 an amino acid residue selected from the group consisting of glutamine residue and asparagine residue;

and wherein the numbering of the amino acid positions refers to the amino acid sequence of wild type SF-rhabdovirus glycoprotein.

18. The polypeptide of any one of clauses 7 to 17, wherein said amino acid sequence of wild type SF-rhabdovirus glycoprotein consists of or is the amino acid sequence of SEQ ID NO:16.

19. The polypeptide of any one of clauses 1 to 18, wherein said ectodomain comprises or consists of an amino acid sequence having at least 70%, preferably at least 80%, more preferably at least 90% or still more preferably at least 95% sequence identity with a sequence selected from the group consisting of SEQ ID NO:1, SEQ ID NO:2 and SEQ ID NO:3.

20. The polypeptide of any one of clauses 1 to 19, wherein said ectodomain comprises or consists of an amino acid sequence having at least 70%, preferably at least 80%, more preferably at least 90% or still more preferably at least 95% sequence identity with the amino acid sequence of SEQ ID NO:1, and wherein said ectodomain has at amino acid position 285 an amino acid residue other than an arginine residue, and/or at amino acid position 282 an amino acid residue other than an arginine residue, and/or at amino acid position 286 an amino acid residue selected from the group consisting of lysine residue, leucine residue, isoleucine residue, valine residue and tryptophane residue, and/or at amino acid position 287 a lysine residue, and has
  at amino acid position 312 an amino acid residue other than an arginine residue, and/or
  at amino acid position 309 an amino acid residue other than an arginine residue, and/or
  at amino acid position 313 an amino acid residue selected from the group consisting of lysine residue, leucine residue, isoleucine residue, valine residue and tryptophane residue, and/or
  at amino acid position 314 a lysine residue,
wherein the numbering of the amino acid positions refers to the amino acid sequence of SEQ ID NO:1.

21. The polypeptide of clause 20, wherein said ectodomain has
  at amino acid position 285 an amino acid residue other than an arginine residue,
and
  at amino acid position 312 an amino acid residue other than an arginine residue,
and wherein the numbering of the amino acid positions refers to the amino acid sequence of SEQ ID NO:1.

22. The polypeptide of any one of clauses 9 to 21, wherein said amino acid residue other than an arginine residue is a naturally occurring, preferably a genetically encoded, amino acid residue,
and/or wherein said amino acid residue other than a basic amino acid residue is a naturally occurring, preferably a genetically encoded, amino acid residue.

23. The polypeptide of any one of clauses 20 to 22, wherein said ectodomain has
  at amino acid position 285 an amino acid residue selected from the group consisting of amino acid residue with a polar but uncharged side chain, amino acid residue with a hydrophobic side chain, and glycine residue
  and/or at amino acid position 282 an amino acid residue selected from the group consisting of amino acid residue with a polar but uncharged side chain, amino acid residue with a hydrophobic side chain, and glycine residue;
and
  at amino acid position 312 an amino acid residue selected from the group consisting of amino acid residue with a polar but uncharged side chain, amino acid residue with a hydrophobic side chain, and glycine residue
  and/or at amino acid position 309 an amino acid residue selected from the group consisting of amino acid residue with a polar but uncharged side chain, amino acid residue with a hydrophobic side chain, and glycine residue;
and wherein the numbering of the amino acid positions refers to the amino acid sequence of SEQ ID NO:1.

24. The polypeptide of clause 23, wherein said amino acid residue with a polar but uncharged side chain is selected from the group consisting of serine residue, threonine residue, tyrosine residue, asparagine residue, and glutamine residue, and/or wherein said amino acid residue with a hydrophobic side chain is selected from the group consisting of alanine residue, valine residue, leucine residue, methionine residue, isoleucine residue, phenylalanine residue, and tryptophan residue.

25. The polypeptide of any one of clauses 20 to 24, wherein said ectodomain has
  at amino acid position 285 an amino acid residue selected from the group consisting of glutamine residue and asparagine residue and/or at amino acid position 282 an amino acid residue selected from the group consisting of glutamine residue and asparagine residue;
and
  at amino acid position 312 an amino acid residue selected from the group consisting of glutamine residue and asparagine residue and/or at amino acid position 309 an amino acid residue selected from the group consisting of glutamine residue and asparagine residue;
and wherein the numbering of the amino acid positions refers to the amino acid sequence of SEQ ID NO:1.

26. The polypeptide of any one of clauses 1 to 25, wherein said ectodomain comprises or consists of an amino acid sequence being 529-550 amino acid residues in length.

27. The polypeptide of any one of clauses 1 to 26, wherein said ectodomain comprises or consists of an amino acid sequence being 529, 530 or 550 amino acid residues in length.

28. The polypeptide of any one of clauses 1 to 27, wherein said ectodomain has the sequence of any one of SEQ ID NO:1 to SEQ ID NO:3.

29. The polypeptide of any one of clauses 1 to 28, wherein the heterologous multimerization domain is selected from the group consisting of immunoglobulin sequence, coiled coil sequence, streptavidin sequence, fibritin sequence, and avidin sequence.

30. The polypeptide of any one of clauses 1 to 29, wherein the heterologous multimerization domain is selected from the group consisting of immunoglobulin constant region domain, leucine zipper domain and *Escherichia* virus T4 fibritin sequence.

31. The polypeptide of any one of clauses 1 to 30, wherein the heterologous multimerization domain is a dimerization domain, preferably selected from the group consisting of IgG Fc domain and leucine zipper domain.

32. The polypeptide of any one of clauses 1 to 31, wherein the heterologous multimerization domain comprises or consists of a IgG Fc domain.

33. The polypeptide of any one of clauses 1 to 32, wherein the heterologous multimerization domain comprises or consists of a guinea pig IgG Fc domain.

34. The polypeptide of any one of clauses 1 to 33, wherein the heterologous multimerization domain comprises or consists of an amino acid sequence having at least 70%, preferably at least 80%, more preferably at least 90%, still more preferably at least 95% or in particular 100% sequence identity with a sequence selected from the group consisting of SEQ ID NO:5, SEQ ID NO:6, SEQ ID NO:7 and SEQ ID NO:8.

35. The polypeptide of any one of clauses 2 to 34, wherein said linker moiety is an amino acid sequence being 1 to 50 amino acid residues in length.

36. The polypeptide of any one of clauses 2 to 35, wherein said linker moiety is an amino acid sequence being 3 to 20 amino acid residues in length.

37. The polypeptide of any one of clauses 2 to 36, wherein said linker moiety comprises or consists of an amino acid sequence having at least 66%, preferably at least 80%, more preferably at least 90%, still more preferably at least 95% or in particular 100% sequence identity with a sequence selected from the group consisting of SEQ ID NO:9, SEQ ID NO:10 and SEQ ID NO:11.

38. The polypeptide of any one of clauses 1 to 37, wherein said polypeptide is a protein comprising or consisting of an amino acid sequence having at least 70%, preferably at least 80%, more preferably at least 90%, still more preferably at least 95% sequence identity with a sequence selected from the group consisting of SEQ ID NO:12, SEQ ID NO:13 and SEQ ID NO:14.
39. The polypeptide of any one of clauses 1 to 38, wherein said polypeptide is a protein comprising an amino acid sequence selected from the group consisting of SEQ ID NO:12, SEQ ID NO:13 and SEQ ID NO:14.
40. The polypeptide of any one of clauses 1 to 39, wherein in a baculovirus expression system the yield of said polypeptide is higher, preferably by at least a factor 2, more preferably by at least a factor 3, still more preferably by at least a factor 5, yet more preferably by at least a factor 8, compared to the yield of the polypeptide of SEQ ID NO:15.
41. The polypeptide of any one of clauses 1 to 40, wherein said polypeptide is a recombinant protein, preferably a recombinant baculovirus expressed protein.
42. A polynucleotide which encodes the polypeptide of any one of clauses 1 to 41.
43. The polynucleotide of clause 42, wherein said polynucleotide comprises a nucleotide sequence having at least 70%, preferably at least 80%, more preferably at least 90%, still more preferably at least 95% or in particular 100% sequence identity with a sequence selected from the group consisting of SEQ ID NO:17, SEQ ID NO:18 and SEQ ID NO:19.
44. A plasmid, preferably an expression vector, comprising a polynucleotide which encodes the polypeptide of any one of clauses 1 to 41.
45. A cell comprising a plasmid, preferably an expression vector, which comprises a polynucleotide encoding the polypeptide of any one of clauses 1 to 41.
46. A baculovirus containing a polynucleotide which encodes the polypeptide of any one of clauses 1 to 41.
47. A cell, preferably an insect cell, infected with a baculovirus which contains a polynucleotide encoding the polypeptide of any one of clauses 1 to 41.
48. The plasmid of clause 44, the cell of clause 45, the baculovirus of clause 46 or the cell of clause 47, wherein said polynucleotide comprises a nucleotide sequence having at least 70%, preferably at least 80%, more preferably at least 90%, still more preferably at least 95% or in particular 100% sequence identity with a sequence selected from the group consisting of SEQ ID NO:17, SEQ ID NO:18 and SEQ ID NO:19.
49. A kit containing the polypeptide of any one of clauses 1 to 41 immobilized to a solid support.
50. A method of producing the polypeptide of any one of clauses 1 to 41, wherein the method comprises
transfecting a cell with a plasmid, preferably an expression vector, which comprises a polynucleotide comprising a sequence which encodes said polypeptide,
or
infecting a cell, preferably an insect cell, with a baculovirus containing a polynucleotide comprising a sequence which encodes said polypeptide.
51. The method of clause 50, wherein said plasmid is the plasmid of clause 44 or 48.
52. The method of clause 50, wherein said baculovirus is the baculovirus of clause 46 or 48.
53. A method of determining in a biological sample obtained from an individual the presence or absence of antibodies specific for a rhabdovirus, comprising the steps of:
a. contacting the biological sample with a capture reagent immobilized to a solid support, wherein the capture reagent is the polypeptide of any of clauses 1 to 41; and
b. determining the presence or absence of said antibodies bound to said capture reagent.
54. The method of clause 53, further comprising the steps of:
c. separating the biological sample from the immobilized capture reagent;
d. contacting the immobilized capture reagent-antibody complex with a detectable agent that binds to the antibody of the reagent-antibody complex; and
e. measuring the level of antibody bound to the capture reagent using a detection means for the detectable agent, and wherein the measuring step (e) preferably further comprises a comparison with a standard curve to determine the level of antibody bound to the capture reagent.
55. Use of the polypeptide of any one of clauses 1 to 41 in a method for determining in a biological sample obtained from an individual the presence or absence of antibodies specific for a rhabdovirus, wherein said method is preferably the method of clause 53 or 54.

The invention claimed is:

1. A polypeptide comprising
   an ectodomain of a rhabdovirus glycoprotein, and
   a heterologous multimerization domain linked to the ectodomain,
   wherein the ectodomain is an ectodomain of a SF-rhabdovirus glycoprotein having
      at amino acid position 306 an amino acid residue other than an arginine residue, and/or
      at amino acid position 303 an amino acid residue other than an arginine residue, and/or
      at amino acid position 305 an amino acid residue other than a basic amino acid residue, and/or
      at amino acid position 307 an amino acid residue selected from the group consisting of lysine residue, leucine residue, isoleucine residue, valine residue and tryptophane residue, and/or
      at amino acid position 308 a lysine residue,
   and having
      at amino acid position 333 an amino acid residue other than an arginine residue, and/or
      at amino acid position 330 an amino acid residue other than an arginine residue, and/or
      at amino acid position 332 an amino acid residue other than a basic amino acid residue, and/or
      at amino acid position 334 an amino acid residue selected from the group consisting of lysine residue, leucine residue, isoleucine residue, valine residue and tryptophane residue, and/or
      at amino acid position 335 a lysine residue,
   and wherein the numbering of the amino acid positions refers to the amino acid sequence of wild type SF-rhabdovirus glycoprotein as set forth in SEQ ID NO:16,
   and wherein the heterologous multimerization domain comprises or consists of a IgG Fc domain.

2. The polypeptide of claim 1,
   wherein said heterologous multimerization domain is linked to said ectodomain via a linker moiety,
   or wherein said heterologous multimerization domain is linked to said ectodomain via a peptide bond between the N-terminal amino acid residue of said heterologous multimerization domain and the C-terminal amino acid residue of said ectodomain.

3. The polypeptide of claim 1, wherein said polypeptide is a fusion protein of the formula x-y-z, wherein
   x consists of or comprises an ectodomain of a rhabdovirus glycoprotein;
   y is a linker moiety; and
   z is a heterologous multimerization domain.

4. The polypeptide of claim 1, wherein said ectodomain is free of a furin cleavage site, and wherein
   said furin cleavage site is an amino acid sequence selected from the group consisting of the following a), b), and c):
   a) amino acid sequence selected from the group consisting of RXKR (SEQ ID NO:20) and RXRR (SEQ ID NO:21);
   b) amino acid sequence selected from the group consisting of $RX_1KRX_2$ (SEQ ID NO:22) and $RX_1RRX_2$ (SEQ ID NO:23), wherein
      $X_1$ can be any amino acid residue, and
      $X_2$ can be any amino acid residue other than
         a lysine residue or
         an amino acid residue selected from the group consisting of valine residue, leucine residue, isoleucine residue and tryptophan residue;
   c) amino acid sequence selected from the group consisting of $RX_1KRX_2X_3$ (SEQ ID NO:24) and $RX_1RRX_2X_3$ (SEQ ID NO:25), wherein
      $X_1$ can be any amino acid residue,
      $X_2$ can be any amino acid residue other than
         a lysine residue or
         an amino acid residue selected from the group consisting of valine residue, leucine residue, isoleucine residue and tryptophan residue,
      and $X_3$ can be any amino residue other than a lysine residue.

5. The polypeptide of claim 1, wherein said ectodomain comprises an amino acid sequence having at least 70%, 80%, 90% or 95% sequence identity with a sequence selected from the group consisting of SEQ ID NO:1, SEQ ID NO:2 and SEQ ID NO:3.

6. The polypeptide of claim 1, wherein said ectodomain comprises or consists of an amino acid sequence having at least 80%, at least 90% or at least 95% sequence identity with the amino acid sequence of SEQ ID NO:1, and wherein said ectodomain has
- at amino acid position 282 an amino acid residue other than an arginine residue and/or
- at amino acid position 286 an amino acid residue selected from the group consisting of lysine residue, leucine residue, isoleucine residue, valine residue and tryptophan residue and/or
- at amino acid position 287 a lysine residue, and has
- at amino acid position 309 an amino acid residue other than an arginine residue and/or
- at amino acid position 313 an amino acid residue selected from the group consisting of lysine residue, leucine residue, isoleucine residue, valine residue and tryptophan residue and/or,
- at amino acid position 314 a lysine residue, wherein the numbering of the amino acid positions refers to the amino acid sequence of SEQ ID NO:1.

7. The polypeptide of claim 1, wherein the heterologous multimerization domain comprises an amino acid sequence having at least 70%, 80%, 90%, 95% or 100% sequence identity with a sequence selected from the group consisting of SEQ ID NO:5, SEQ ID NO:6, SEQ ID NO:7 and SEQ ID NO:8.

8. The polypeptide of claim 1, wherein said linker moiety is an amino acid sequence being 1 to 50 amino acid residues in length,
and/or wherein said linker moiety comprises or consists of an amino acid sequence having at least 66%, 80%, 90%, 95% or 100% sequence identity with a sequence selected from the group consisting of SEQ ID NO:9, SEQ ID NO:10 and SEQ ID NO:11.

9. The polypeptide of claim 1, wherein said polypeptide is a protein comprising a sequence selected from the group consisting of SEQ ID NO:12, SEQ ID NO:13 and SEQ ID NO:14.

10. A polynucleotide that encodes the polypeptide of claim 1,
wherein said polynucleotide comprises a nucleotide sequence having at least 70%, 80%, 90%, 95% or in particular 100% sequence identity with a sequence selected from the group consisting of SEQ ID NO:17, SEQ ID NO:18 and SEQ ID NO:19.

11. A plasmid expression vector comprising the polynucleotide of claim 10.

12. An isolated A cell comprising the plasmid expression vector of claim 11
or
an insect cell infected with a baculovirus that contains the polynucleotide of claim 10.

13. A baculovirus containing the polynucleotide of claim 10.

14. A kit containing the polypeptide of claim 1 immobilized to a solid support.

15. A method of producing the polypeptide of claim 1, wherein the method comprises either:
1) Transfecting a cell with a plasmid expression vector, which comprises a polynucleotide comprising a sequence which encodes said polypeptide, and wherein said plasmid is the plasmid of claim 11
or
2) infecting an insect cell with the baculovirus of claim 13.

16. A method of determining in a biological sample obtained from a subject for the presence or absence of antibodies specific for a rhabdovirus, comprising the steps of:
a) contacting the biological sample with a capture reagent immobilized to a solid support, wherein the capture reagent is the polypeptide of claim 1 and wherein said rhabdovirus glycoprotein ectodomain is homologous to the rhabdovirus to be detected; and
b) determining the presence or absence of said antibodies bound to said capture reagent.

* * * * *